US012059199B2

(12) United States Patent
Shin et al.

(10) Patent No.: US 12,059,199 B2
(45) Date of Patent: *Aug. 13, 2024

(54) STENT DELIVERY SYSTEM COMPRISING MONOPOLAR ELECTROCAUTERY TIP

(71) Applicant: TAEWOONG MEDICAL CO., LTD, Gimpo-si (KR)

(72) Inventors: Kyong Min Shin, Yangpyeong-gun (KP); Kwang Seok Kim, Bucheon-si (KR); Se Ik Park, Gwanak-gu (KR); Seong Wook Park, Paju-si (KR)

(73) Assignee: TAEWOONG MEDICAL CO., LTD, Gimpo-si (KR)

( * ) Notice: Subject to any disclaimer, the term of this patent is extended or adjusted under 35 U.S.C. 154(b) by 1195 days.

This patent is subject to a terminal disclaimer.

(21) Appl. No.: 16/347,000

(22) PCT Filed: Nov. 14, 2017

(86) PCT No.: PCT/KR2017/012870
§ 371 (c)(1),
(2) Date: May 2, 2019

(87) PCT Pub. No.: WO2018/093114
PCT Pub. Date: May 24, 2018

(65) Prior Publication Data
US 2019/0254741 A1   Aug. 22, 2019

(30) Foreign Application Priority Data
Nov. 16, 2016   (KR) .................. 10-2016-0152644

(51) Int. Cl.
*A61B 18/14*   (2006.01)
*A61F 2/95*   (2013.01)
(Continued)

(52) U.S. Cl.
CPC ............ *A61B 18/1492* (2013.01); *A61F 2/95* (2013.01); *A61F 7/12* (2013.01);
(Continued)

(58) Field of Classification Search
CPC ...... A61B 18/1492; A61B 2018/00083; A61B 2018/00214; A61B 2018/00595;
(Continued)

(56) References Cited

U.S. PATENT DOCUMENTS 7,758,625 B2   7/2010   Fitzgerald et al.
9,452,069 B2   9/2016   Argentine et al.
(Continued)

FOREIGN PATENT DOCUMENTS

EP   2851024 A1   3/2015
EP   3417836 A1   12/2018
(Continued)

OTHER PUBLICATIONS

International Search Report for PCT/KR2017/012870 dated Mar. 20, 2018.

*Primary Examiner* — Jaymi E Della
*Assistant Examiner* — Abigail M Ziegler
(74) *Attorney, Agent, or Firm* — Bridgeway IP Law Group, PLLC; Jihun Kim

(57) ABSTRACT

The present disclosure relates to a stent delivery system, and can be configured to include a connector portion connected to an external current source, an electrocautery tip connected to the connector portion by a conductive line, and a delivery portion having one side connected to the electrocautery tip, having the other side connected to the connector portion, and having the conductive line for connecting the electrocautery tip and the connector portion positioned therein, and a stent space portion in which a stent is positioned is formed adjacent to the electrocautery tip inside the delivery portion, (Continued)

and the delivery portion gradually moves and supplies the stent into the human body tissue, and according to the present disclosure, it is possible to integrate the conductive line and the tube, thereby improving the rigidity of the tube, and varying the size of the electrocautery tip.

20 Claims, 20 Drawing Sheets

(51) Int. Cl.
  *A61F 7/12* (2006.01)
  *A61B 18/00* (2006.01)
  *A61B 18/12* (2006.01)
  *A61F 2/966* (2013.01)
(52) U.S. Cl.
  CPC .............. *A61B 2018/00083* (2013.01); *A61B 2018/00214* (2013.01); *A61B 2018/00595* (2013.01); *A61B 2018/1253* (2013.01); *A61F 2/9517* (2020.05); *A61F 2/966* (2013.01)
(58) Field of Classification Search
  CPC .... A61B 2018/1253; A61F 2/95; A61F 2/966; A61F 2/962; A61F 7/12; A61F 2/9517; A61F 2002/9511; A61F 2007/126
  See application file for complete search history.

(56) References Cited

U.S. PATENT DOCUMENTS

| | | | | |
|---|---|---|---|---|
| 10,118,015 | B2* | 11/2018 | de la Rama | A61M 25/0052 |
| 2006/0111704 | A1 | 5/2006 | Brenneman et al. | |
| 2011/0066148 | A1* | 3/2011 | Hamou | A61B 18/1485 606/41 |
| 2012/0046657 | A1* | 2/2012 | Biadillah | A61B 18/1492 606/33 |
| 2013/0131667 | A1* | 5/2013 | Jenson | A61B 18/1492 606/41 |
| 2013/0310833 | A1 | 11/2013 | Binmoeller et al. | |
| 2014/0261985 | A1* | 9/2014 | Selkee | A61M 25/0009 156/187 |
| 2015/0133925 | A1 | 5/2015 | Chen et al. | |
| 2015/0133927 | A1 | 5/2015 | Shin et al. | |
| 2015/0342770 | A1* | 12/2015 | Howard | A61F 2/958 623/23.7 |
| 2016/0066976 | A1 | 3/2016 | Motai | |
| 2016/0242846 | A1* | 8/2016 | Brown | A61B 17/320016 |

FOREIGN PATENT DOCUMENTS

| | | |
|---|---|---|
| JP | 2000-287992 A | 10/2000 |
| JP | 2000287992 A | 10/2000 |
| JP | 20010510354 A | 7/2001 |
| JP | 2005511199 A | 4/2005 |
| JP | 2010512858 A | 4/2010 |
| JP | 2015093193 A | 5/2015 |
| JP | 2015-518741 A | 7/2015 |
| JP | 2015521065 A | 7/2015 |
| KR | 20100086294 A | 7/2010 |
| KR | 20130140954 A | 12/2013 |
| KR | 101493766 B1 | 2/2015 |
| KR | 20150052475 A | 5/2015 |
| WO | 97/45157 A1 | 12/1997 |
| WO | 2008/051941 A2 | 5/2008 |
| WO | 2015/023075 A1 | 2/2015 |
| WO | 2015/107802 A1 | 7/2015 |
| WO | 2017/142236 A1 | 8/2017 |

* cited by examiner

STENT DELIVERY SYSTEM COMPRISING MONOPOLAR ELECTROCAUTERY TIP

RELATED APPLICATIONS

The present invention is a U.S. National Stage under 35 USC 371 patent application, claiming priority to Serial No. PCT/KR2017/012870, filed on 14 Nov. 2017; which claims priority of KR 10-2016-0152644, filed on 16 Nov. 2016, the entirety of both of which are incorporated herein by reference.

TECHNICAL FIELD

The present disclosure relates to a stent delivery system.

BACKGROUND ART

A stent is an endoprostheses device that is used to secure a circulatory passage of blood, body fluid, food, body waste, etc. by inserting it into a blocked area in a human body.

The stent is mainly made of a plastic material or a metal material. First, there is a problem in that the plastic material with a thin diameter can be easily inserted, while due to its material property and thin diameter, the self-expansion is collapsed and the stent treatment area is blocked again.

Therefore, in the medical field, the stent of a metal material is used in many cases. The metal material is expensive but basically has an inherent rigidity, such that even if intermittent muscle contraction or external shock applied in the body tissue of the stent treatment area, etc. occurs, it is temporarily contracted but is self-expanded again, thereby efficiently keeping the function thereof.

Recently, when problems such as occlusion and damage have occurred on the circulatory passage of the human body, such as blood vessel, ureter, and bile duct, a non-surgical method is preferred rather than a surgical method as before, and as a part of this trend, the stent treatment is being activated.

A stent delivery system such as a catheter is used to insert the stent into the body tissue area to be treated.

Herein, in simply explaining the stent delivery system, the stent delivery system is basically configured to include an electrocautery tip, an insertion tube, a stent, a handle, a current connector, etc.

The current connector is a part that is connected to an external current source such as an electric treatment instrument to receive a current for heating, and the electrocautery tip is a part that is connected to the current connector by a conductive line to form a hole by receiving a current to cauterize the body tissue.

Then, the insertion tube is generally made of an insulating material, and the stent is embedded inside the insertion tube, such that the practitioner inserts the insertion tube into the body tissue through a cauterization hole by the operation of the handle, and positions the stent at the area to be treated.

Thereafter, the stent is exposed from the insertion tube through the operation of the handle and the stent is self-expanded, thereby solving occlusion, damage, etc. of the treatment area.

However, in the conventional stent delivery system, since the insertion tube is made of an insulating material, when a practitioner, such as a doctor or a nurse, accidentally applies an impact by incorrect use, the phenomenon that is easily bent or deflected occurs easily. In extreme cases, a problem that is broken due to external damage also occurs.

If such problems occur during the actual treatment, it can result in a fatal medical accident for the person to be treated, such as a patient.

The insertion tube is inserted into the human body, such that some flexibility thereof should be ensured, and in addition, it is a part touching the human body, such that the insulation property should be electrically kept. Therefore, in the stent treatment technology field, there is a demand for a tube with the enhanced durability in order not to be easily damaged even by the carelessness of the practitioner, such as a doctor or a nurse, while keeping the basic characteristics of the above-mentioned insertion tube. Of course, the position of the conductive line connected to the electrocautery tip should be also considered adequately.

In addition, there is a problem in that most of stent delivery systems currently used have a fixed size of the electrocautery tip, such that the size of the cauterization hole cannot be adjusted according to the treatment environment in the body tissue of the person to be treated. This results in the limitation that cannot adequately cope with a change in the variable treatment environment.

Therefore, in order to provide more advanced treatment environment, there is a demand for a treatment device that can variably adjust the cauterization hole in the body tissue for delivering various types of stents required in the treatment area of the body tissue.

Technical Problem

The present disclosure is intended to solve the above problems of the relate art, and an object of the present disclosure is to provide an apparatus configured to integrate a conductive line and a tube, thereby improving the rigidity of the tube, and varying the size of an electrocautery tip.

Technical Solution

The present disclosure for achieving the object relates to a stent delivery system, and can be configured to include a connector portion connected to an external current source, an electrocautery tip connected to the connector portion by a conductive line, and a delivery portion having one side connected to the electrocautery tip, having the other side connected to the connector portion, and having the conductive line for connecting the electrocautery tip and the connector portion positioned therein, and a stent space portion in which a stent is positioned is formed adjacent to the electrocautery tip inside the delivery portion, and the delivery portion gradually moves and supplies the stent into the human body tissue.

In addition, in an embodiment of the present disclosure, the delivery portion can include a first internal tube having the conductive line connected to the electrocautery tip positioned therein, and having an inner hole formed at the internal central side thereof, a second internal tube positioned to surround a portion of the outer circumference of the first internal tube, and provided to be connected to the first internal tube to be integrally moved, and an external tube positioned to surround the second internal tube.

In addition, in an embodiment of the present disclosure, the first internal tube can be an insulating coating material, and the conductive line can be formed integrally with the first internal tube and positioned in a straight-line form along the longitudinal direction of the first internal tube.

In addition, in an embodiment of the present disclosure, the first internal tube can be an insulating coating material, and the conductive line can be formed integrally with the first internal tube and positioned to be wound in a spiral direction along the circumference of the first internal tube.

In addition, in an embodiment of the present disclosure, the first internal tube can be an insulating coating material, and the conductive line can be formed integrally with the first internal tube and positioned in a woven form along the circumference of the first internal tube.

In addition, in an embodiment of the present disclosure, the delivery portion can further include a first grip portion connected to the external tube and a second grip portion connected to the second internal tube by a movable bar, and the connector portion is positioned on the second grip portion, and the first internal tube is positioned by passing through the movable bar and the second grip portion.

In addition, in an embodiment of the present disclosure, the electrocautery tip can include a tip electrode body having a tip guide hole, which is passed through, formed therein, having one side portion of the outer circumferential surface tapered in one direction, and having the other side portion of the outer circumferential surface connected to the conductive line and a tip insulator having one side connected to the other side portion of the tip electrode body, and having the other side connected to the delivery portion.

In addition, in an embodiment of the present disclosure, one side of the tip insulator can be configured to be tapered in the same direction as the tip electrode body, and the other side of the tip insulator can be configured to be tapered in the direction opposite to one side of the tip insulator.

In addition, in an embodiment of the present disclosure, the tip electrode body and the tip insulator can be provided in a triangular form that a side cross-sectional surface thereof is inclined in the same direction.

In addition, in an embodiment of the present disclosure, the electrocautery tip can further include a coupling portion formed at a portion of the outer circumference of the tip electrode body and a variable ring connected to the coupling portion to vary the size of the tip electrode body.

In addition, in an embodiment of the present disclosure, a portion of the outside of the variable ring can be tapered in the same direction as the tip electrode body.

In addition, in an embodiment of the present disclosure, a portion of the outside of the variable ring can be tapered at an angle smaller than the tip electrode body.

In addition, in an embodiment of the present disclosure, the outer circumference of the variable ring can be round-processed.

In addition, in an embodiment of the present disclosure, a portion of the variable ring can have a different thickness.

In addition, in an embodiment of the present disclosure, the electrocautery tip can further include an adhesion pad positioned on at least any one side of the coupling portion in order to prevent a gap between the inner circumference of the variable ring and the outer circumference of the tip electrode body.

In addition, in an embodiment of the present disclosure, the electrocautery tip can further include a cauterization protrusion formed at the outer circumference of the tip electrode body.

In addition, in an embodiment of the present disclosure, the cauterization protrusion can be positioned in plural with predetermined intervals interposed therebetween on the outer circumference of the tip electrode body.

In addition, in an embodiment of the present disclosure, the cauterization protrusion can be a straight-line form.

In addition, in an embodiment of the present disclosure, the cauterization protrusion can be a curved form.

In addition, in an embodiment of the present disclosure, the plurality of cauterization protrusions can be insulation-coated therebetween in the tip electrode body.

In addition, in an embodiment of the present disclosure, the stent delivery system with the mono-polar electrocautery tip can further include a guide wire positioned in an inner hole of the first internal tube and a tip guide hole of the tip electrode body, and for guiding the moving direction of the electrocautery tip.

In addition, in an embodiment of the present disclosure, the delivery portion can further include a moving adjustment unit for gradually adjusting the movement of the movable bar, and the moving adjustment unit can include an uneven portion formed along the longitudinal direction of the movable bar and a fixing portion positioned inside the first grip portion in order to be coupled to the uneven portion and gradually fix the movement of the movable bar.

In addition, in an embodiment of the present disclosure, the fixing portion can include an elastic body positioned inside the first grip portion and a fixing block having one side closely contacting the elastic body, and having the other side protruded to a first inner hole.

In addition, in an embodiment of the present disclosure, the fixing portion can further include a rolling wheel rotatably positioned on the fixing block.

In addition, in an embodiment of the present disclosure, the tip guide hole can be eccentrically positioned inside the tip electrode body.

Advantageous Effects

According to the present disclosure, it can be expected to enhance the rigidity of the tube by integrating the conductive wire and the tube positioned at the innermost portion thereof. At this time, the form that the conductive wire is positioned to be spirally wound in plural and the form that is positioned to be connected by the repetitive woven structure further enhance the rigidity as the entire tube.

In addition, it is possible to change the size, that is, the diameter of the electrocautery tip, thereby appropriately adjusting the size that forms the hole in the human body according to the size of the treatment area, the cross-sectional size of the tube, the degree of expansion and contraction of the stent, etc.

In addition, it can be additionally expected to minimize the incision area of the human body tissue through the structure, which provides the electrocautery protrusion pattern to the electrocautery tip, and applies the current only to the pattern area.

BEST MODE

Hereinafter, preferred embodiments of a stent delivery system according to the present disclosure will be described in detail with reference to the accompanying drawings.

Figure 1:
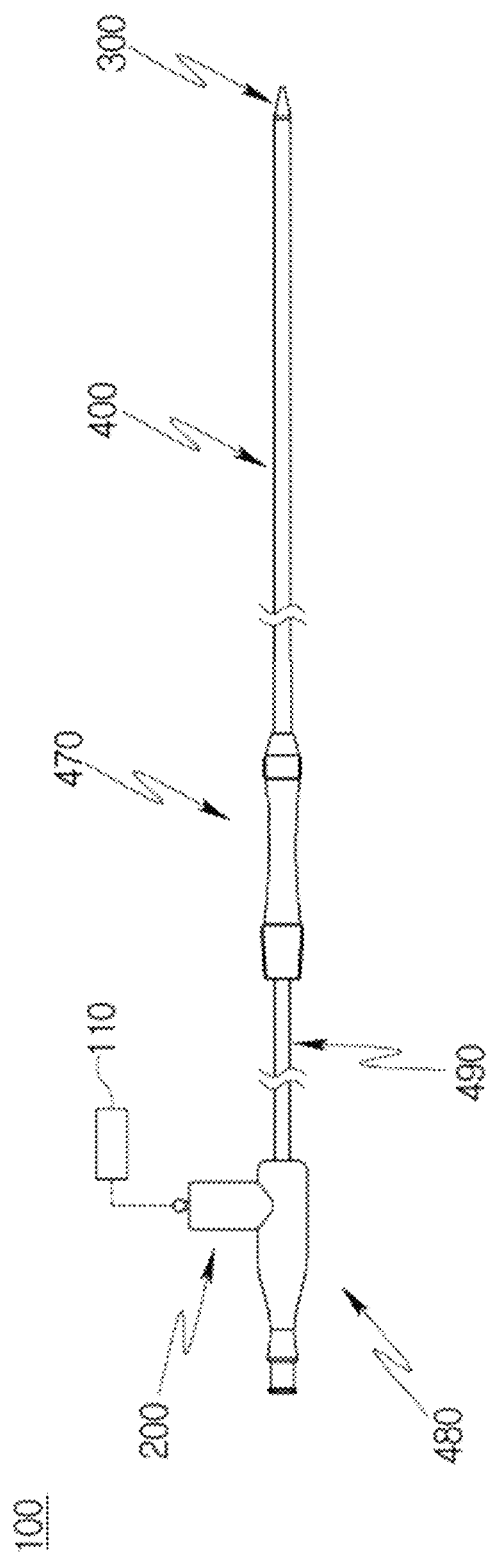
FIG. 1 is an external diagram of a stent delivery system of the present disclosure.
Figure 2:
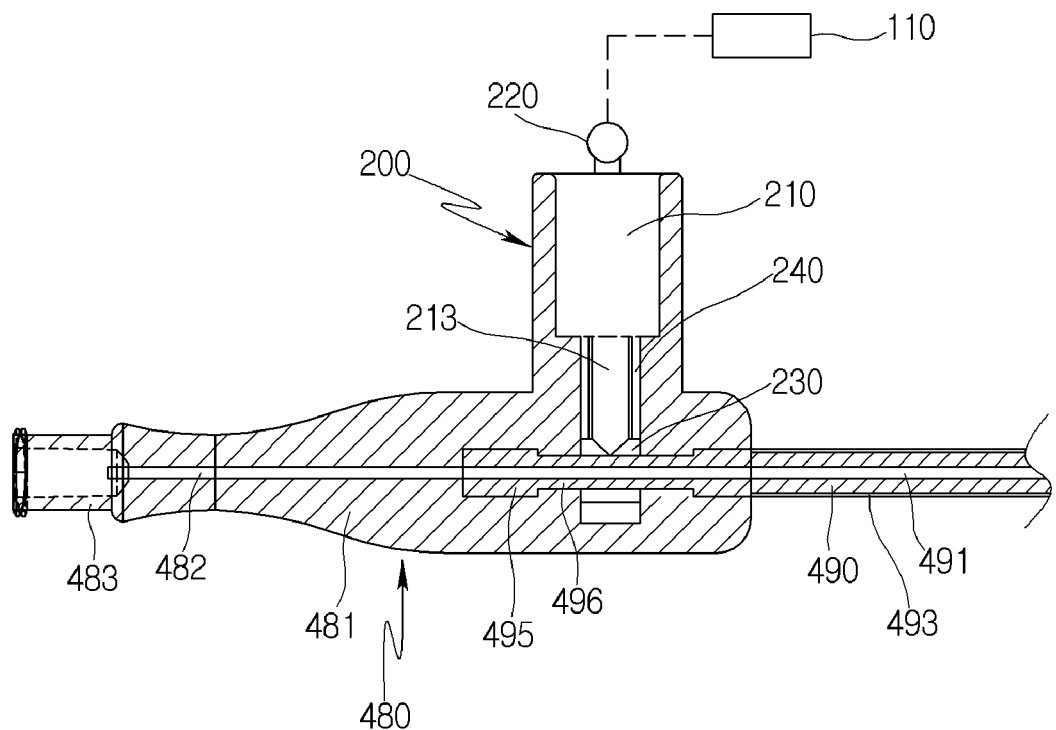
FIG. 2 is a side cross-sectional diagram illustrating a connector portion and a second grip portion in the disclosure illustrated in FIG. 1.
Figure 4:
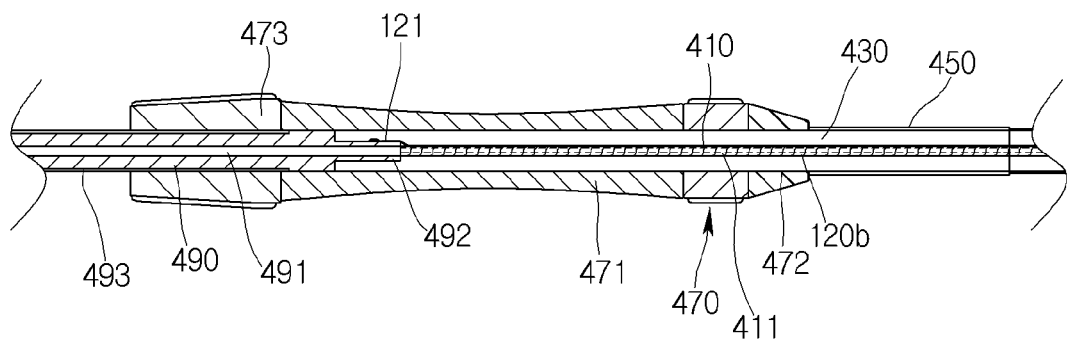
Figure 5:
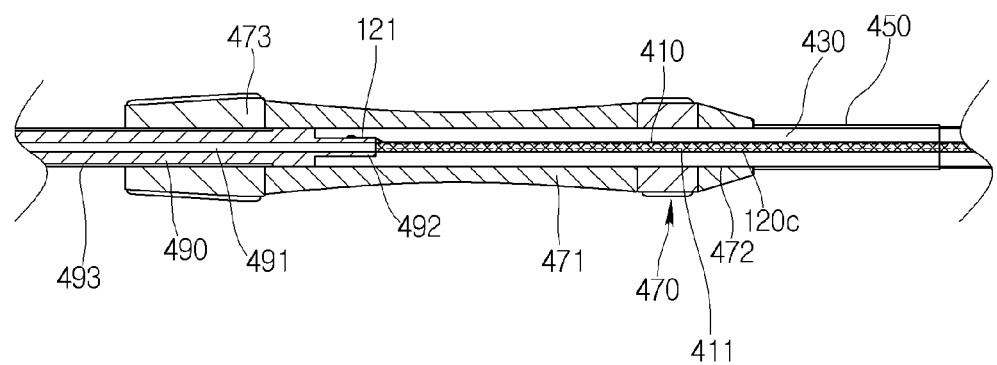
Figure 6:
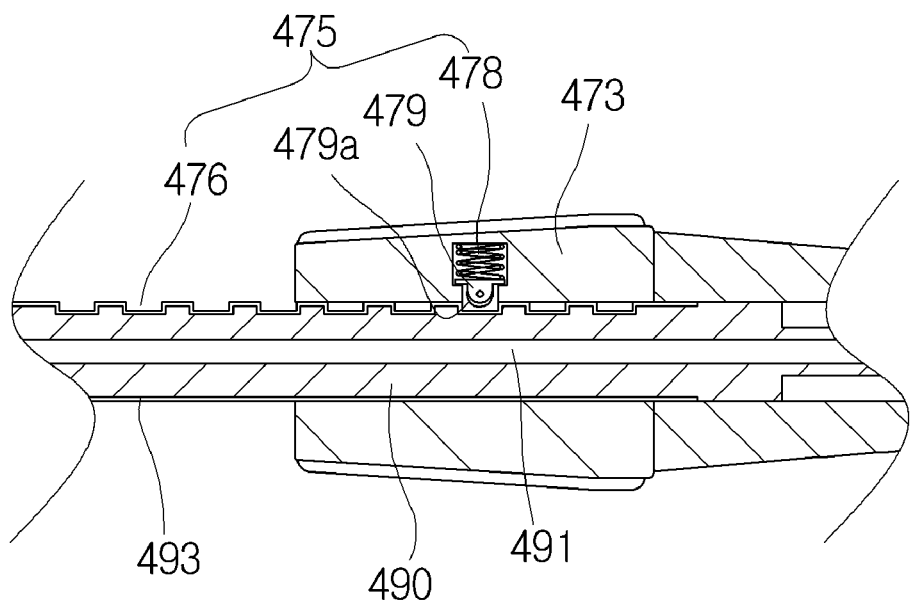
FIG. 6 is a side cross-sectional diagram illustrating the first grip portion and a moving adjustment unit in the disclosure illustrated in FIG. 1.
Figure 7:
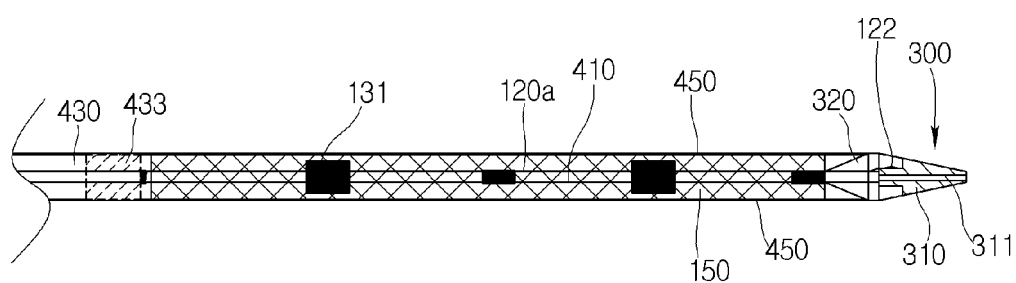
FIG. 7 is a side cross-sectional diagram illustrating an electrocautery tip and a stent space portion in the disclosure illustrated in FIG. 1.
Figure 8:
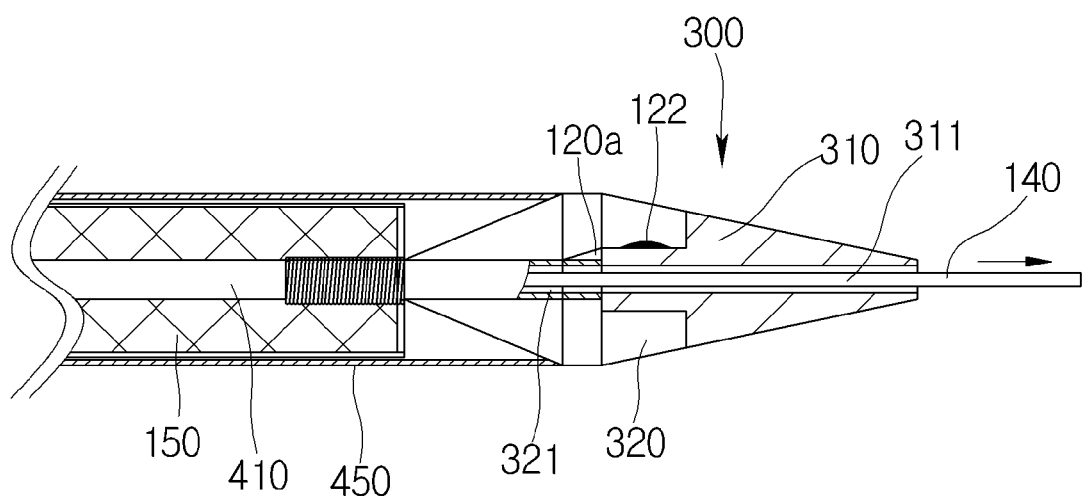
FIGS. 8 and 9 are side cross-sectional diagrams illustrating a first embodiment of the electrocautery tip of the present disclosure.
Figure 9:
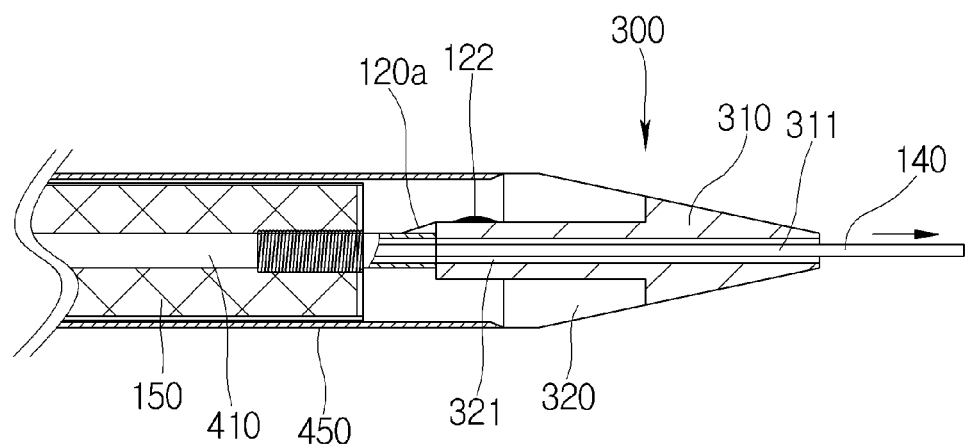
Figure 10:
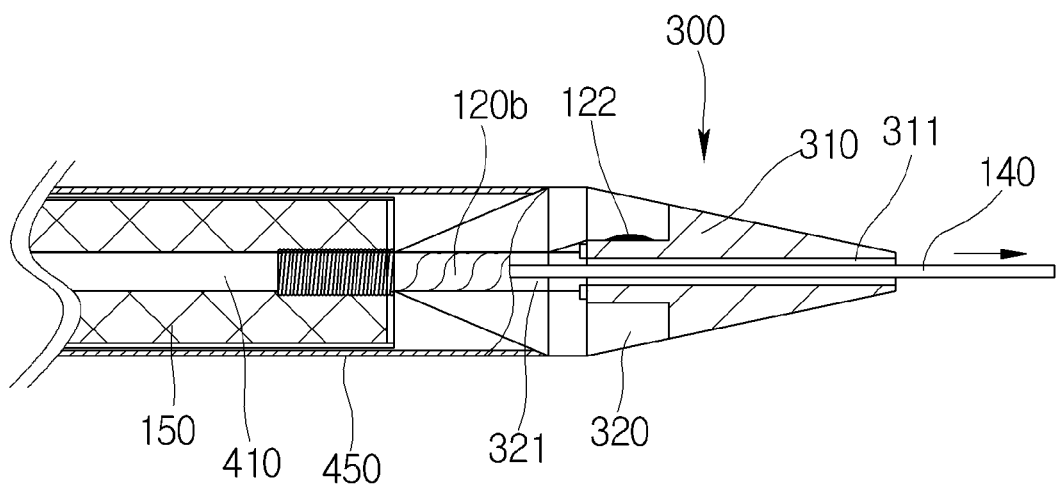
FIG. 10 is a side cross-sectional diagram illustrating another form that connects the conductive line of the electrocautery tip of the present disclosure.
Figure 11:
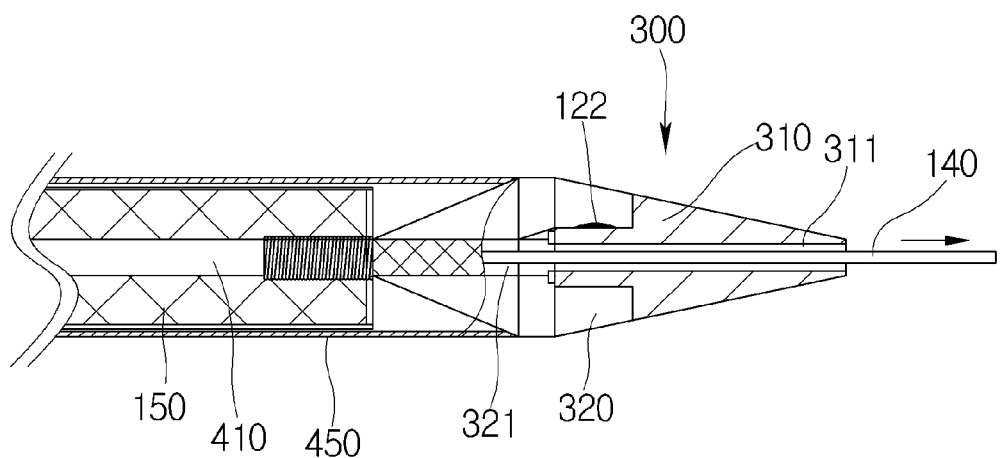
FIG. 11 is a side cross-sectional diagram illustrating still another form that connects the conductive line of the electrocautery tip of the present disclosure.
Figure 12:
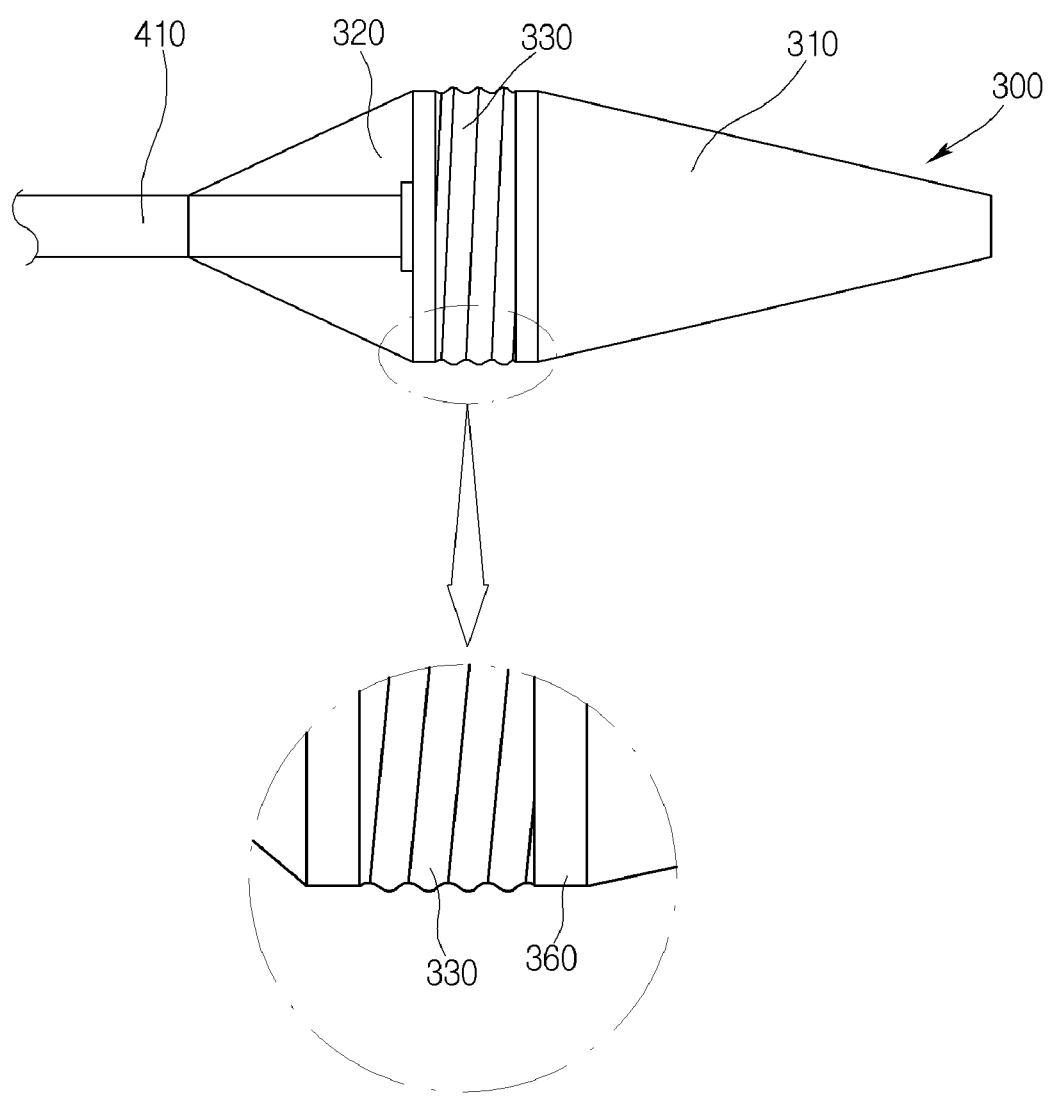
FIG. 12 is a side cross-sectional diagram illustrating a second embodiment of the electrocautery tip of the present disclosure.
Figure 13:
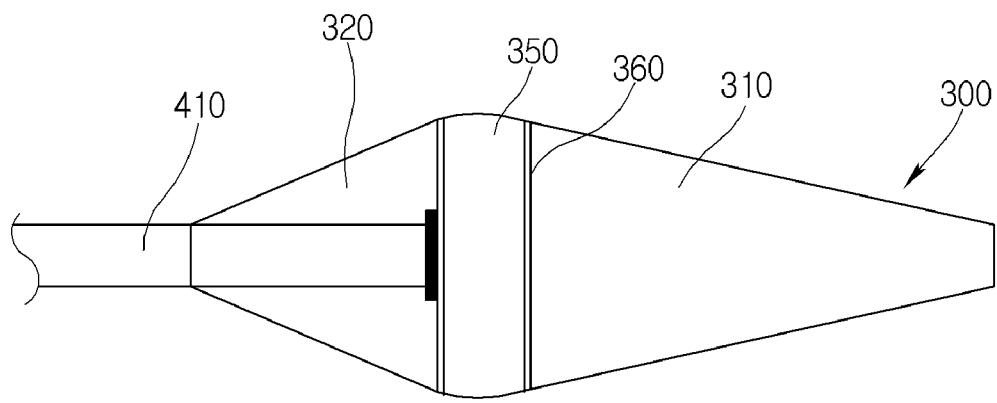
FIG. 13 is a side cross-sectional diagram illustrating a state where a variable ring has been mounted thereon in the disclosure illustrated in FIG. 12.
Figure 14:
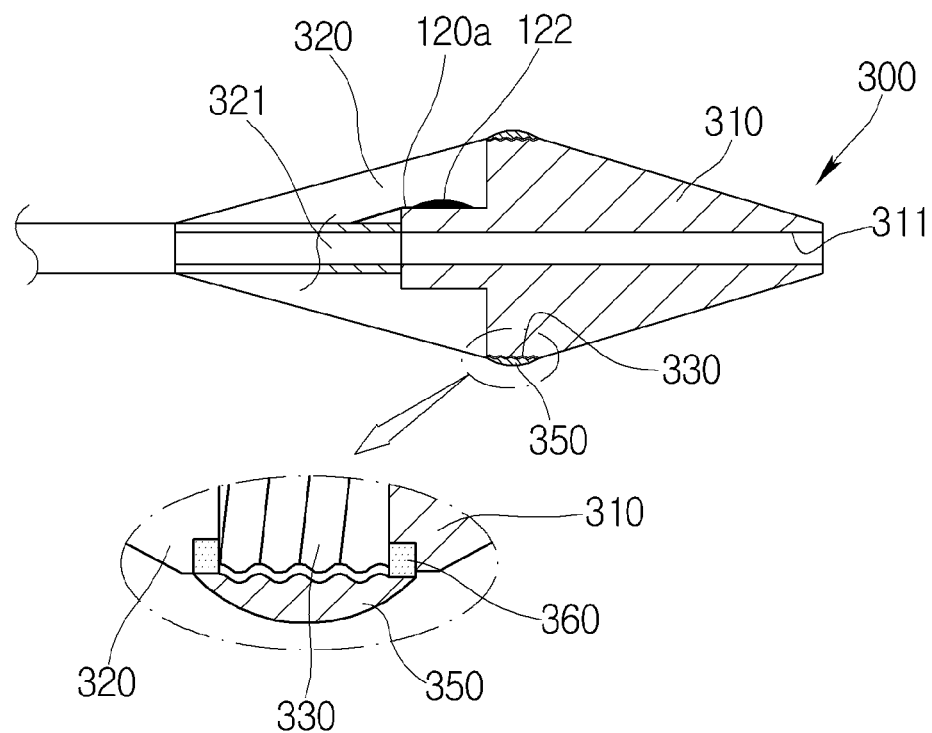
FIG. 14 is a side cross-sectional diagram illustrating one form of the variable ring in the disclosure illustrated in FIG. 13.
Figure 15:
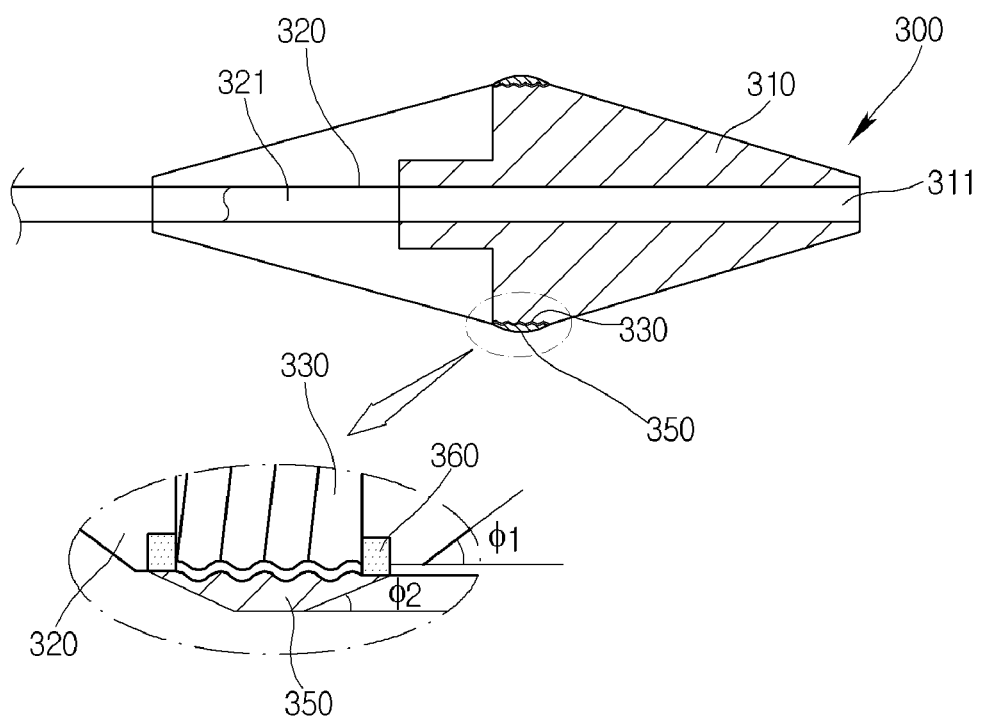
FIG. 15 is a side cross-sectional diagram illustrating another form of the variable ring in the disclosure illustrated in FIG. 13.
Figure 18:
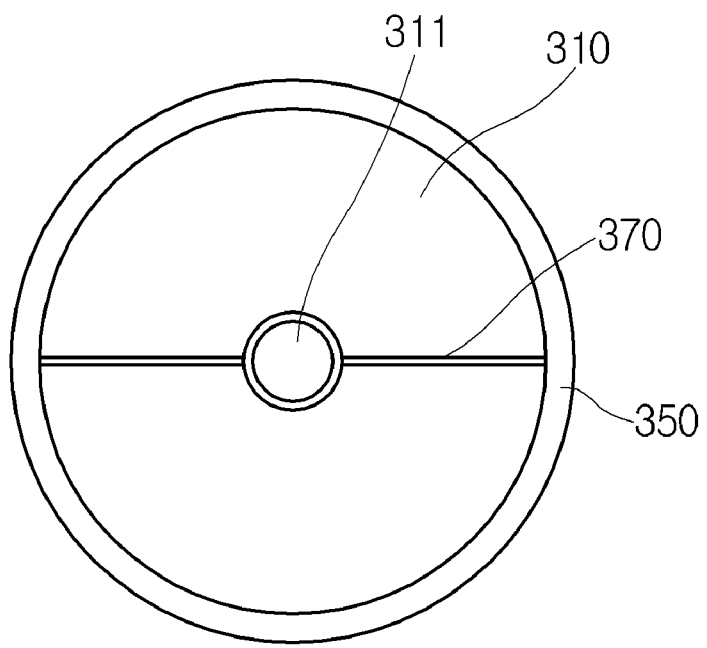
Figure 19:
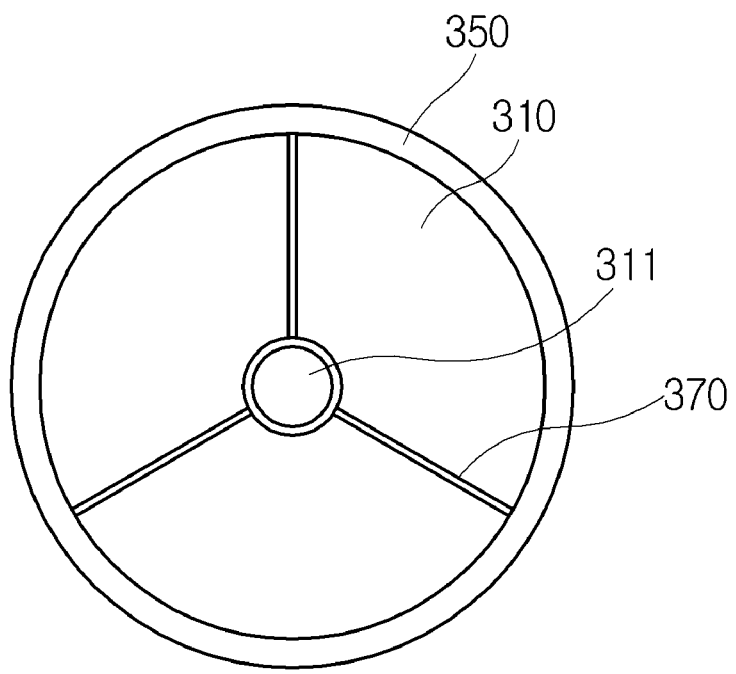
Figure 20:
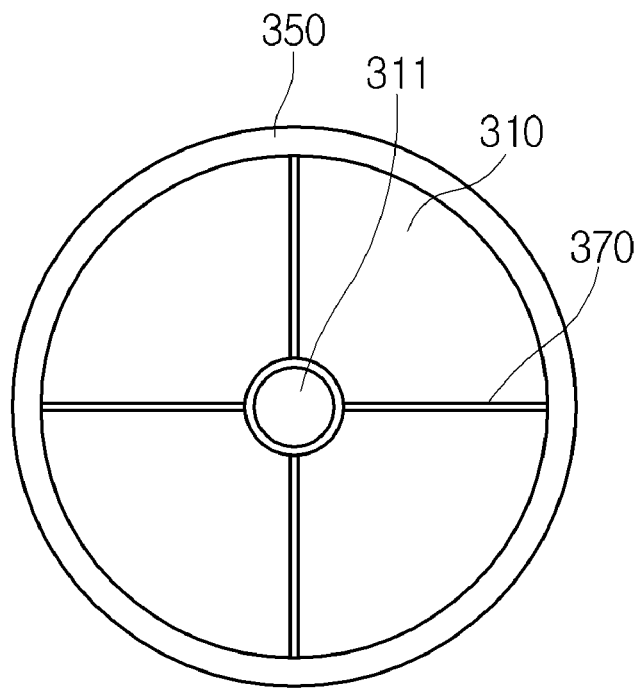
Figure 21:
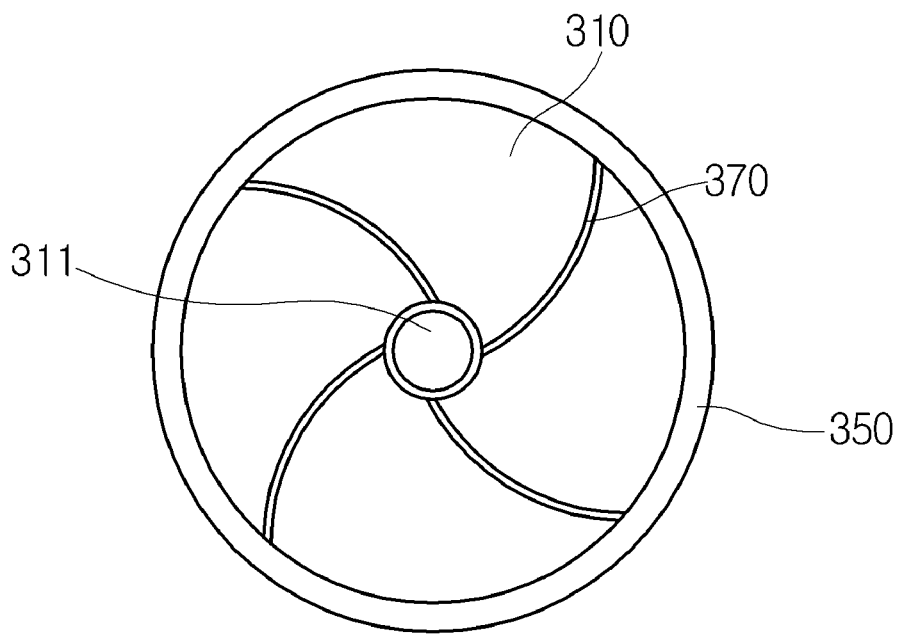
Figure 22:
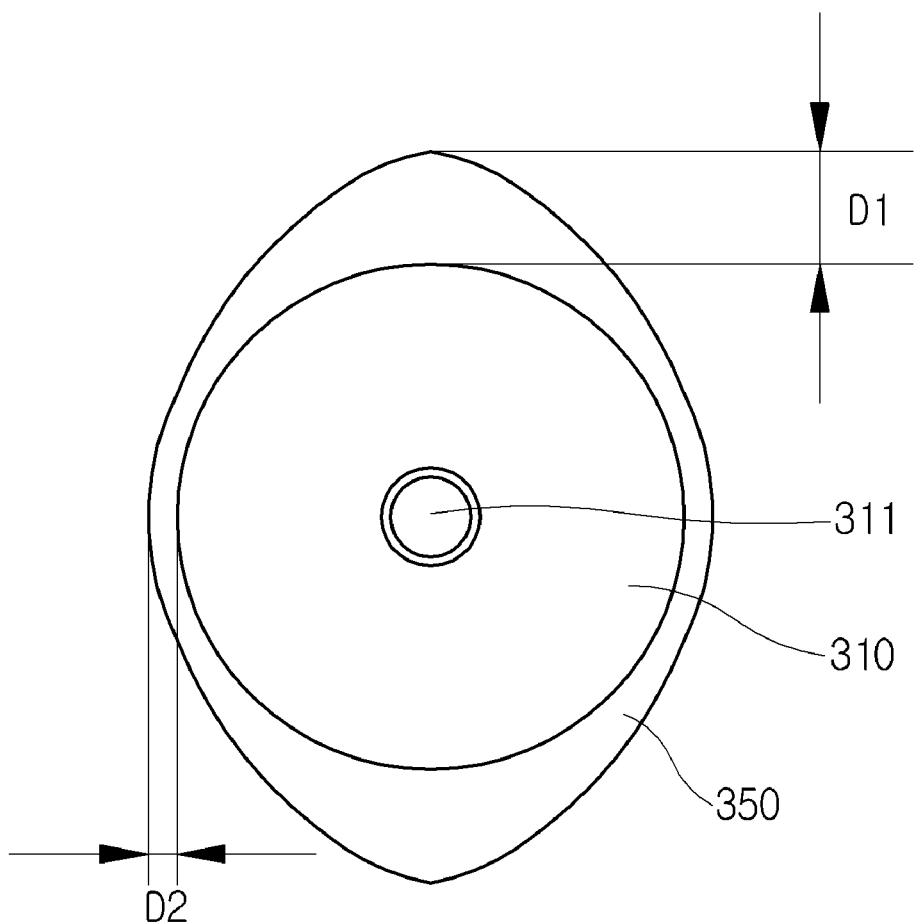
Figure 23:
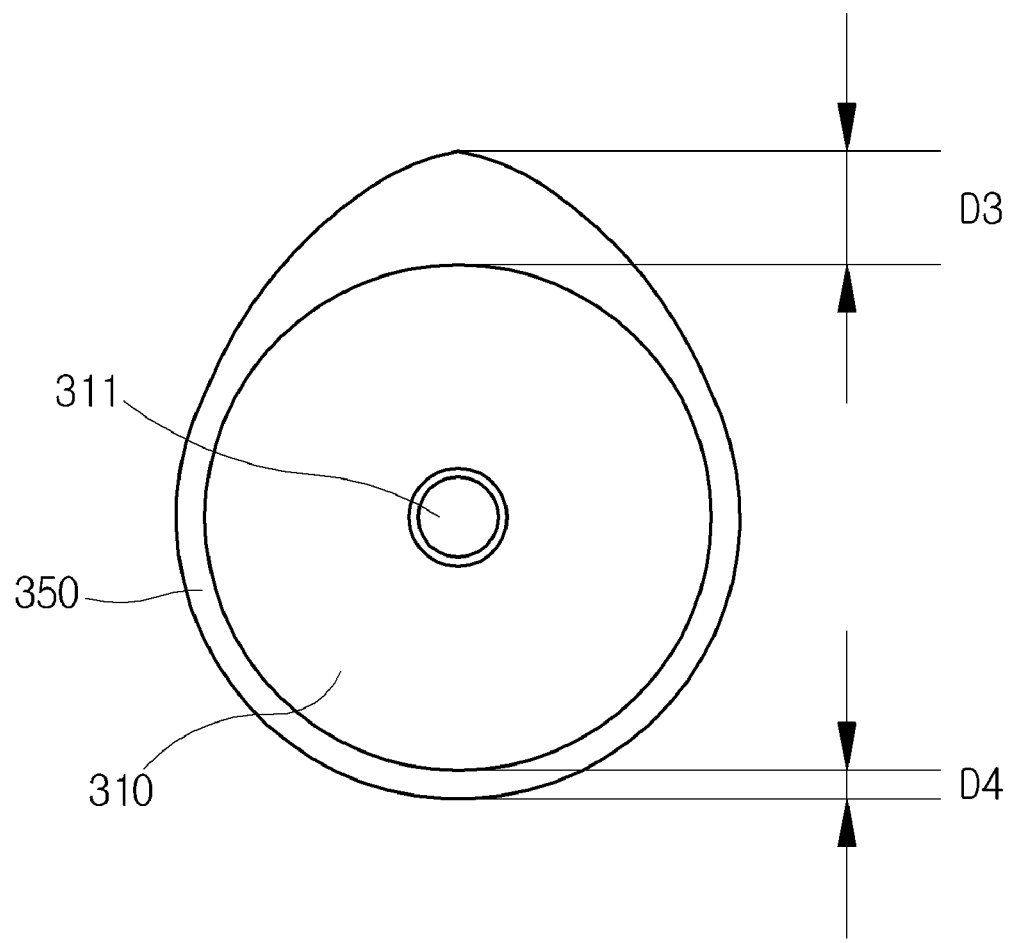
Figure 24:
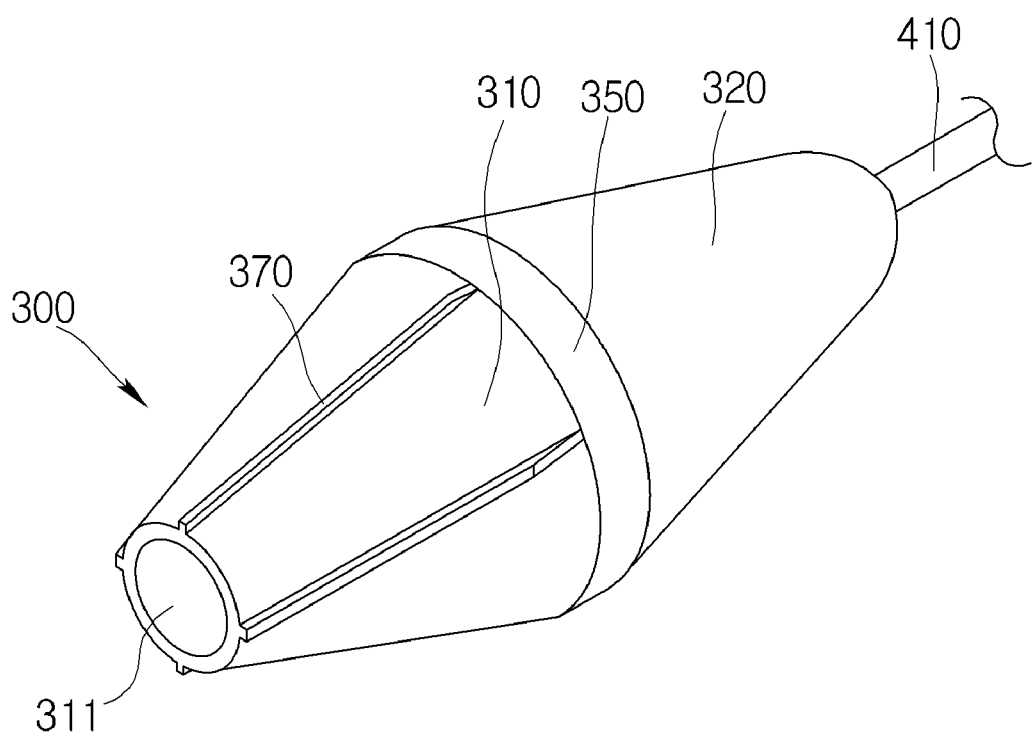
FIG. 24 is a partial perspective diagram of the disclosure illustrated in FIG. 20.

FIG. 1 is an external diagram of a stent delivery system of the present disclosure, FIG. 2 is a side cross-sectional diagram illustrating a connector portion and a second grip portion in the disclosure illustrated in FIG. 1, FIGS. 3 to 5 are side cross-sectional diagrams illustrating forms of a first grip portion and a conductive line in the disclosure illustrated in FIG. 1, FIG. 6 is a side cross-sectional diagram illustrating the first grip portion and a moving adjustment unit in the disclosure illustrated in FIG. 1, FIG. 7 is a side cross-sectional diagram illustrating an electrocautery tip and a stent space portion in the disclosure illustrated in FIG. 1, FIGS. 8 and 9 are side cross-sectional diagrams illustrating a first embodiment of the electrocautery tip of the present disclosure, FIG. 10 is a side cross-sectional diagram illustrating another form that connects the conductive line of the electrocautery tip of the present disclosure, FIG. 11 is a side cross-sectional diagram illustrating still another form that connects the conductive line of the electrocautery tip of the present disclosure, FIG. 12 is a side cross-sectional diagram illustrating a second embodiment of the electrocautery tip of the present disclosure, FIG. 13 is a side cross-sectional diagram illustrating a state where a variable ring has been mounted thereon in the disclosure illustrated in FIG. 12, FIG. 14 is a side cross-sectional diagram illustrating one form of the variable ring in the disclosure illustrated in FIG. 13, FIG. 15 is a side cross-sectional diagram illustrating another form of the variable ring in the disclosure illustrated in FIG. 13, FIGS. 16 to 23 are diagrams illustrating various forms of the electrocautery protrusions that are positioned at the tip electrode body and the variable rings of the present disclosure, FIG. 24 is a partial perspective diagram of the disclosure illustrated in FIG. 20.

Referring to FIGS. 1 to 23, a stent delivery system 100 of the present disclosure can be configured to include a connector portion 200, an electrocautery tip 300, and a delivery portion 400.

First, referring to FIG. 2, the connector portion 200 can be a portion electrically connected to an external current source 110. Herein, the external current source 110 can be a high frequency generator or a low frequency generator, but is not necessarily limited thereto.

The connector portion 200 can be made of a conductive material such as a metal material. Then, the connector portion 200 can have a connection protrusion 220 functioning as a terminal for connecting a connector body 210 and the external current source 110 formed at one side portion of the connector body 210, and have a screw pin 213 positioned at the other side portion thereof in order to be screw-fastened and coupled to a connection beam 240. Then, the connection beam 240 can be formed with a through-hole 230 to which a movable bar 490, which will be described below, is connected.

Herein, an end block 495 is processed at the end portion of the movable bar 490, and the end block 495 can be formed to have the diameter greater than a stepped portion 496 of the movable bar 490.

At this time, the through-hole 230 is processed to have the diameter through which the end block 495 can pass, and when the connector body 210 is further rotated after the end block 495 is fitted and passed through, the screw pin 213 is rotated down to the stepped portion 496.

Through such a structure, the movable bar 490 is not detached from a second grip portion 480 even when it is pulled excessively. This is because the end block 495 is blocked and not pulled out by the lower end of the screw pin 213 inside the through-hole 230.

The connector portion 200 can be provided to be fixed to a second grip body 481 of the second grip portion 480, which will be described below. A wire outlet 483 can be positioned at the end portion of the second grip body 481.

Next, the delivery portion 400 can be a portion that has one side connected to the electrocautery tip 300, and has the other side connected to the connector portion 200. The delivery portion 400 can be configured to include a first internal tube 410, a second internal tube 430, an external tube 450, a first grip portion 470, the second grip portion 480, and the movable bar 490.

Hereinafter, the insulating material used in the present disclosure can be urethane, polyester, polyimide, other plastic materials, ceramic, silicone, fluorine resin, teflon, etc., but is not necessarily limited thereto. Such an insulating material can be selectively applied to various tubes, insulating coating materials, tip insulators, etc., which will be described below.

Referring to FIGS. 2 to 7, the first internal tube 410 is a portion that is positioned at the innermost portion in the delivery portion 400, and a conductive line 120 connected to the electrocautery tip 300 can be positioned therein.

The first internal tube 410 can be divided into three forms according to the positional form of the conductive line 120.

Figure 3:
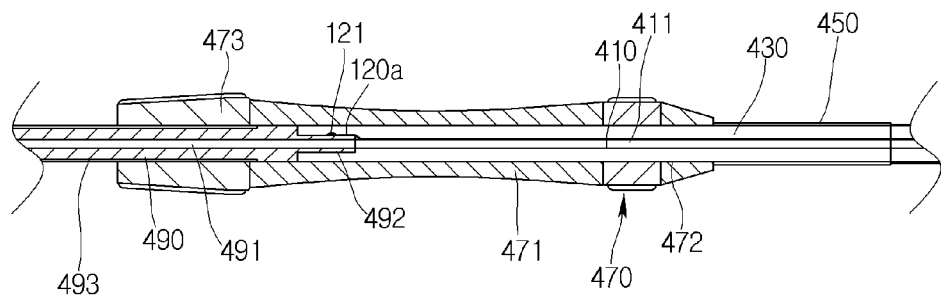
FIGS. 3 to 5 are side cross-sectional diagrams illustrating forms of a first grip portion and a conductive line in the disclosure illustrated in FIG. 1.

First, referring to FIG. 3, one form of the first internal tube 410 is disclosed. In this form, the first internal tube 410 is provided with an insulating coating material, and a conductive line 120a is formed integrally with the first internal tube 410 and positioned in a straight-line form along the internal longitudinal direction of the first internal tube 410.

Specifically, the conductive line 120a is positioned in parallel along the external longitudinal direction of the first internal tube 410 that is an insulating coating material, and can be a structure that insulation-coats the first internal tube 410 and the conductive line 120a together once again at the external portion thereof.

For another example, the first internal tube 410 has an inner hole 411 formed at the internal central side thereof, and for this purpose, should have a constant thickness, and the conductive line 120a can be a structure that is positioned at the thickness portion to be insulation-processed together.

Of course, it is not necessarily limited to the above structure, and other structures capable of keeping the insulating property are also possible.

Then, a portion, which contacts the movable bar 490, of the end portion of the conductive line 120a can be welded-coupled 121 and fused by resistance welding, laser welding, or non-soldering, and electrically connected thereto. Of course, it is not necessarily limited thereto, and it is also possible to connect in the method of knotting one end portion of the conductive line 120a after processing the through-hole in the movable bar 490, or other connection methods other than the above are also possible.

A portion, which contacts the electrocautery tip 300, of the end portion of the conductive line 120a can also be welded-coupled 122 and fused and electrically connected to a tip electrode body 310 as in FIG. 8, and of course, is not limited to the connection method.

At this time, the movable bar 490 can be made of a conductive material such as a metal material, and can be formed with a stepped portion whose diameter is slightly reduced along the outer circumference of a portion, which is exposed between the first grip portion 470 and the second grip portion 480, of a portion of the movable bar 490 and an insulating material that is a bar insulator 493 can be applied to the stepped portion in order to prevent the electric shock of a practitioner.

The bar insulator 493 can be a polytetrafluoroethylene (PTFE) coating material. This is excellent in chemical resistance, heat resistance, etc., and can be suitable as an insulating material for the medical instruments using electricity.

Of course, it is not necessarily limited to the above structure, and other structures capable of keeping the insulating property are also possible.

Next, referring to FIG. 4, another form of the first internal tube 410 is disclosed. In this form, the first internal tube 410 is provided with an insulating coating material, and a conductive line 120b is formed integrally with the first internal tube 410 and positioned in a form wound in a spiral direction along the circumference of the first internal tube 410.

At this time, the conductive line 120b can be made of a metal material, and the conductive line 120b is positioned at the first internal tube 410 while being wound in plural times, thereby improving the rigidity of the first internal tube 410.

Accurately, the inner hole 411 is formed at the internal central side of the first internal tube 410, and for this purpose, the first internal tube 410 has a constant thickness. The conductive line 120b is positioned at the thickness portion, and therefore, the conductive line 120b is entirely surrounded by an insulating coating material and positioned while being wound in plural times in a spiral direction along the circumference of the first internal tube 410.

Then, a portion, which contacts the movable bar 490, of the end portion of the conductive line 120b protruded from the end portion of the first internal tube 410 can be welded-coupled 121 and electrically connected thereto. Of course, it is not necessarily limited thereto, and it is also possible to connect in the method of knotting by protruding a portion of the conductive line 120b from the end portion of the first internal tube 410 after processing the through-hole in the movable bar 490, and other connection methods other than the above are also possible.

In addition, a portion, which contacts the electrocautery tip 300, of the end portion of the conductive line 120b can also be welded-coupled 122 and electrically connected to the tip electrode body 310 as in FIG. 10, but is not necessarily limited to the connection method.

Next, referring to FIG. 5, still another form of the first internal tube 410 is disclosed. In this form, the first internal tube 410 is provided with an insulating coating material, and a conductive line 120c is formed integrally with the first internal tube 410 and positioned in a woven form along the circumference of the first internal tube 410.

At this time, the conductive line 120c can be made of a metal material, and the conductive line 120c is repeatedly positioned at the first internal tube 410 in a woven form, thereby improving the rigidity of the first internal tube 410.

Accurately, the inner hole 411 is formed at the internal central side of the first internal tube 410, and for this purpose, the first internal tube 410 has a constant thickness. The conductive line 120c is positioned at the thickness portion, and therefore, the conductive line 120c is entirely surrounded by an insulating coating material and positioned in a repetitive woven form along the circumference of the first internal tube 410.

Then, a portion, which contacts the movable bar 490, of the end portion of the conductive line 120c protruded from the end portion of the first internal tube 410 can be welded-coupled 121 and electrically connected thereto. Of course, it is not necessarily limited thereto, and it is also possible to connect in the method of knotting by protruding a portion of the conductive line 120c from the end portion of the first internal tube 410 after processing the through-hole in the movable bar 490, and other connection methods other than the above are also possible.

In addition, a portion, which contacts the electrocautery tip 300, of the end portion of the conductive line 120c can also be welded-coupled 122 and electrically connected to the tip electrode body 310 as in FIG. 11, but is not necessarily limited to the connection method.

Next, referring to FIGS. 1, 3, and 7, the second internal tube 430 can be positioned to surround a portion of the outer circumference of the first internal tube 410, and provided to be connected to the first internal tube 410 to move integrally. The second internal tube 430 can be made of an insulating material.

First, referring to FIG. 7, it can be confirmed that the second internal tube 430 is positioned to surround a portion of the outer circumference of the first internal tube 410, and at this time, a sign block 433 pushing the stent 150 is positioned at the end portion of the second internal tube 430.

Referring to FIG. 3, it can be confirmed that the second internal tube 430 is positioned inside the external tube 450, and fitted into and connected to the outer circumference of a tube connection portion 492 of the movable bar 490, and the first internal tube 410 positioned therein is fitted into and connected to the through-hole of the tube connection portion 492 of the movable bar 490.

Therefore, when the practitioner moves the movable bar 490, the first internal tube 410 connected to the movable bar 490 and the second internal tube 430 integrally move together in the moving direction of the movable bar 490.

Next, referring to FIGS. 1, 3, and 7, the external tube 450 can be a portion that is positioned to surround the second internal tube 430 and connected and fixed to the end portion of the first grip portion 470. That is, since the external tube 450 is fixed to the first grip portion 470, it does not move according to the movement of the movable bar 490, but guides and supports the movement of the first internal tube 410 and the second internal tube 430. The external tube 450 can be made of an insulating material.

Referring to FIG. 7, it can be seen that the stent 150 can be positioned in a non-expansion state in a stent space portion 130 formed by the first internal tube 410 and the external tube 450. That is, the stent 150 is positioned along the circumference of a portion, which is surrounded and not supported by the second internal tube 430, of the first internal tube 410, and the stent 150 keeps the non-expansion state while contacting the inner circumferential surface of the external tube 450.

At this time, a stent support block 131 can be positioned at the outer circumferential surface of the first internal tube 410.

Next, referring to FIG. 3, the first grip portion 470 is a portion that is connected to the end portion of the external tube 450, and can be a portion for the practitioner to grip in order to move the movable bar 490.

A fixing handle 473 can be positioned at one side portion of the first grip portion 470. When the practitioner wishes to restrict the movement of the movable bar 490 after moving the movable bar 490, the practitioner can rotate the fixing handle 473 in one direction. Although not illustrated in the drawing, when the fixing handle 473 is rotated in one direction, the movable bar 490 is pressed to restrict the movement of the movable bar 490. Conversely, when the practitioner wishes to move the movable bar 490 again, the practitioner can rotate the fixing handle 473 in the opposite direction to loosen the pressure on the movable bar 490.

The fixing handle 473 is provided to allow the stent 150 to be positioned at the accurate body tissue area when the stent 150 has been adjacent to the body tissue area to be expanded. This is because if the movable bar 490 moves during the treatment, the position of the stent 150 can be incorrectly positioned.

Meanwhile, in the present disclosure, another form for fixing the movable bar 490 is disclosed. Referring to FIG. 6, the delivery portion 400 can be configured to further include a moving adjustment portion 475 for gradually adjusting the movement of a first grip body 471 that moves along the movable bar 490. Conversely, this can gradually adjust the movement of the movable bar 490 through the relationship with the first grip body 471.

The moving adjustment unit 475 can be configured to include an uneven portion 476 and a fixing portion. First, the uneven portion 476 can be formed in plural with a bent shape along the longitudinal direction of the movable bar 490. Then, the fixing portion can be positioned inside the first grip portion 470 in order to gradually fix the movement of the first grip body 471 that moves along the movable bar 490 while being coupled to the uneven portion 476.

Specifically, the fixing portion can be configured to include an elastic body 478 and a fixing block 479. The elastic body 478 can be positioned in an internal space 471a formed inside the first grip portion 470. The elastic body 478 can be the form such as a coil spring or a plate spring, but when an elastic force can be provided, it is not necessarily limited thereto.

Then, the fixing block 479 can be implemented as a form that has one side closely contacting the elastic body 478 and has the other side protruded to a first inner hole 472. At this time, when the practitioner pulls or pushes the movable bar 490, a rolling wheel 479a can be positioned at the fixing block 479 in order to go beyond the bent shape of the uneven portion 476 relatively and easily.

The gradual movement of the movable bar 490 through the above structure enables the stable gradual self-expansion of the stent in the treatment area of the body tissue when the practitioner actually performs the stent treatment.

The completeness of the stent treatment can be changed according to the treatment environment, the skill of the practitioner, etc. If the practitioner is immature, he/she forcibly pulls the movable bar 490 or the movable bar 490 shakes during the pulling, such that the vibration can be delivered to the stent, thereby not smoothly performing the self-expansion of the stent.

At this time, if the movable bar 490 can be gradually moved and fixed, the movement of the external tube 450 can also be adjusted clearly and gradually as the movable bar 490 is pulled, such that the stent is also exposed slowly and gradually. This induces the accurate self-expansion of the stent, and also enhances the treatment effect. It is also possible to slightly mitigate and prevent the carelessness of the practitioner.

Next, referring to FIG. 8, a first embodiment of the electrocautery tip 300 can be configured to include the tip electrode body 310 and a tip insulator 320.

The tip electrode body 310 can be configured to have a tip guide hole 311, in which a guide wire 140 is inserted and positioned, formed at the central side thereof, have one side portion of the outer circumferential surface tapered in one direction, and have the other side portion of the outer circumferential surface welded-coupled 122 and connected to the conductive line 120. Of course, it is not necessarily limited thereto, and although not illustrated in the drawing, for example, a structure of forming the through-hole and tying and connecting the conductive line 120 in a knotting method is also possible.

The tip electrode body 310 can entirely have a circular cross-sectional shape, and the tip electrode body 310 can be a conductive material such as a metal material as a portion that forms a hole by receiving a current to apply heat to the body tissue. For example, it can be a metal material such as stainless or Ni+Ti alloy.

Next, it can be configured so that one side of the tip insulator 320 is connected to the other side portion of the tip electrode body 310, and the other side thereof is connected to the end portion of the first internal tube 410 of the delivery portion 400. The tip insulator 320 can be an insulating material so that a current does not flow.

Then, the tip insulator 320 can be coated on the tip electrode body 310 in a molding method. In an embodiment of the present disclosure, as illustrated in FIG. 9, the tip insulator 320 and the tip electrode body 310 can be implemented in a form having the side cross-sectional diagram of triangle. Of course, the tip insulator 320 and the tip electrode body 310 can be a shape that is tapered in the same direction when viewed from the front thereof.

In this case, the first internal tube 410 can be formed as a structure that is directly adhered to the tip electrode body rather than the tip insulator, and the electrocautery tip 300 can be easily inserted into the body tissue with the above form.

Alternatively, as illustrated in FIGS. 8, 10, and 7, which are another embodiment of the present disclosure, it can also be implemented in a form that has one portion tapered in the same direction as the tip electrode body 310, and has the other portion tapered in the direction opposite to the tip electrode body 310.

In the case that the tip insulator 320 has a tapered form, when the electrocautery tip 300 is pulled out again after delivering the stent 150 in the body tissue, this operation can be performed relatively and easily.

The body tissue is mainly made of protein, such that even if a cauterization hole is formed by the electrocautery tip 300, the cauterization hole becomes narrow due to the flexibility of the body tissue.

At this time, if the tip insulator 320 has been tapered in the direction opposite to the tip electrode body 310, the cauterization hole widens while spreading along the tapered shape when the practitioner pulls out the electrocautery tip 300 through the cauterization hole, such that the electrocautery tip 300 is easily pulled out.

In this case, the first internal tube 410 is inserted into the tip insulator 320 and adhered to the tip electrode body 310.

Of course, the tip insulator 320 is not necessarily limited to the above forms.

Herein, as another form of a structure of the conductive line 120 connected to the tip electrode body 310, as illustrated in FIG. 10, the conductive line 120 positioned in a spiral form along the circumference of the first internal tube 410 can be used. In this case, the first internal tube 410 itself is made of a flexible insulating material, but the conductive line 120 of a conductive metal material is wound along the circumference thereof, thereby improving the rigidity of the first internal tube 410.

In addition, as still another form of a structure of the conductive line 120 connected to the tip electrode body 310, as illustrated in FIG. 11, the conductive line 120 positioned in a woven form along the circumference of the first internal tube 410 can be used. In this case, the first internal tube 410 made of an insulating material can be prevented from being broken or stretched during use due to its flexibility. That is, this is because the conductive line 120 made of a conductive metal material is positioned in a woven form along the circumference of the first internal tube 410, thereby improving the rigidity of the first internal tube 410.

Meanwhile, referring to FIGS. 12 to 15, a second embodiment of the electrocautery tip 300 can be configured to include the tip electrode body 310, the tip insulator 320, the coupling portion 330, and a variable ring 350.

The tip electrode body 310 can be configured to have the tip guide hole 311, in which the guide wire 140 is inserted and positioned, formed at the central side thereof, have one side portion of the outer circumferential surface tapered in one direction, and have the other side portion of the outer circumferential surface welded-coupled 122 and connected to the conductive line 120. Of course, it is not necessarily limited thereto, and although not illustrated in the drawing, for example, a structure of forming the through-hole and tying and connecting the conductive line 120 in a knotting method is also possible.

The tip electrode body 310 can entirely have a circular cross-sectional shape, and the tip electrode body 310 can be a conductive material such as a metal material as a portion that forms a hole by receiving a current to apply heat to the body tissue.

Then, the coupling portion 330 can be positioned at a portion of the outer circumferential surface of the tip electrode body 310. In an embodiment of the present disclosure, the coupling portion 330 can be provided in a thread form, but since it is a portion that contacts the body tissue, the protruded portion of the thread can be provided to be smoothly round-processed in order to prevent fine damage of the body tissue.

The variable ring 350 can be a portion connected to the coupling portion 330 in order to vary the diameter of the tip electrode body 310. The variable ring 350 can be in a circular ring form, and a thread corresponding to the thread of the coupling portion 330 can be processed at the inner circumferential surface thereof, and provided to be smoothly round-processed as well. The variable ring 350 can be made of the same material as the tip electrode body 310, and that is, can be a conductive metal material. The variable ring 350 also forms a hole in the body tissue.

As an example of the variable ring 350, as illustrated in FIG. 14, it can be a form that the outer circumferential surface of the variable ring 350 has been rounded. In this case, when heat is applied to the body tissue to form a hole and the tip electrode body 310 enters into the body tissue or exits therefrom after the treatment of the stent 150, the tip electrode body 310 can enter into or exit from the body tissue more smoothly without damage on the body tissue due to the round-processed outer circumferential surface. Of course, since the variable ring 350 closely contacts and is electrically connected to the tip electrode body 310, it is also possible to adjust a range of the diameter that forms a hole in the body tissue.

For example, when the practitioner wishes to reduce the size of a hole in the body tissue, the tip electrode body 310 can be used in a state where the variable ring 350 has been separated, and conversely, when the practitioner wishes to form a slightly larger hole at the area of the body tissue to which the stent 150 is to be delivered, the tip electrode body 310 can be used with the variable ring 350 fitted therein.

In an embodiment of the present disclosure, although only one round-processed variable ring 350 has been disclosed, the round-processed shape of the variable ring 350 can be more various, and other shapes can also be included naturally as long as it is within a range that can be inferred from the present disclosure.

In addition, as another example of the variable ring 350, as illustrated in FIG. 15, it can be implemented as a form that the outer circumferential surface of the variable ring 350 has been tapered. At this time, one side of the outer circumferential surface of the variable ring 350 can be processed in a shape tapered in the same direction as the tip electrode body 310, and the other side of the outer circumferential surface of the variable ring 350 can be processed in a shape tapered in the same direction as the tip insulator 320.

In this case, when entering into the body tissue or exiting from it after the treatment of the stent 150, the variable ring 350 has been tapered in the same direction as the tip electrode body 310 or the tip insulator 320, thereby preventing the problem of being caught by the hole formed in the body tissue and causing damage.

Of course, the variable ring 350 closely contacts and is electrically connected to the tip electrode body 310, thereby also adjusting a range of the diameter that forms a hole in the body tissue. A detailed description thereof is as described above.

Although only one taper-processed variable ring 350 has been disclosed in an embodiment of the present disclosure, the taper-processed shape of the variable ring 350 can be more various, and other forms can also be included naturally as long as it is within a range that can be inferred from the present disclosure.

In addition, in an embodiment of the present disclosure, one side of the outer circumferential surface of the variable ring 350 can be processed to be tapered at an angle smaller than that of the tip electrode body 310, and the other side of the outer circumferential surface of the variable ring 350 can be processed to be tapered at an angle smaller than that of the tip insulator 320.

Even if the variable ring 350 is mounted at the tip electrode body 310 through the above processing, the size of the cauterization hole in the body tissue due to the heat caused by the conducted current can be further reduced. Of course, it is possible to reduce not only the size of the cauterization hole simply but also to expand it conversely. The practitioner can have the variable rings 350 having a taper angle in plural, and the variable ring 350 can be used by changing and coupling therewith according to the size of the hole of the body tissue to be cauterized.

Meanwhile, referring to FIGS. 14 and 15, an adhesion pad 360 can be positioned at least any one side of the coupling portion 330 in order to prevent a gap between the inner circumference of the variable ring 350 and the outer circumference of the tip electrode body 310.

In an embodiment of the present disclosure, the adhesion pad 360 is positioned at both sides of the coupling portion 330. The adhesion pad 360 can be entirely a ring shape, and positioned by being forcibly fitted along the outer circumferential surface of the tip electrode body 310. The adhesion pad 360 can be a flexible insulating material slightly protruded outwardly from the coupling portion 330.

The position of the adhesion pad 360 allows the practitioner to closely contact them such an extent that there is no gap therebetween after rotating and fitting the variable ring 350 into the coupling portion 330. This is because when the tip electrode body 310 enters into or exits from the body tissue, it is possible to block the phenomenon that blood, tissue, etc. are flowed and fitted into the spaced interval between the variable ring 350 and the tip electrode body 310.

That is, since the variable ring 350 and the tip electrode body 310 are both made of a metallic material, it is difficult to fit therein perfectly and mechanically, and a minute gap is generated. The gap is blocked by the adhesion pad 360, thereby helping the precision of the human body medical instrument.

Meanwhile, referring to FIGS. 22 and 23, in an embodiment of the present disclosure, the variable ring 350 can be provided to have different thicknesses from each other. For example, first, referring to FIG. 22, when the cauterization hole formed in the body tissue is required to have an elliptical shape, the variable ring 350, which has been formed so that the thickness D1 of one portion thereof is thicker than the thickness D2 of another portion thereof, is mounted thereon and used.

If the hole to be cauterized requires having any one portion protruded, as illustrated in FIG. 23, the variable ring 350, which has been formed so that the thickness D3 of any one portion of the variable ring 350 is thicker than the thickness D4 of another portion thereof, is mounted thereon and used.

Although only two shapes of the variable rings 350 has been illustrated in FIGS. 22 and 23, it will be apparent that the variable ring 350, which has been formed to have various thicknesses that can be inferred within a range having the same object, can be included therein.

Figure 16:
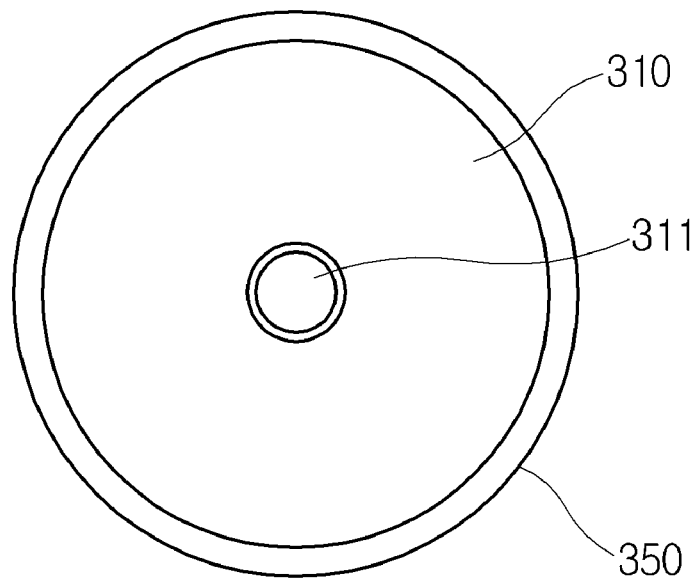
FIGS. 16 to 23 are diagrams illustrating various forms of the electrocautery protrusions that are positioned at the tip electrode body and the variable rings of the present disclosure.

FIG. 16 illustrates a shape of the tip electrode body 310 according to the present disclosure when viewed from the front thereof.

Figure 17:
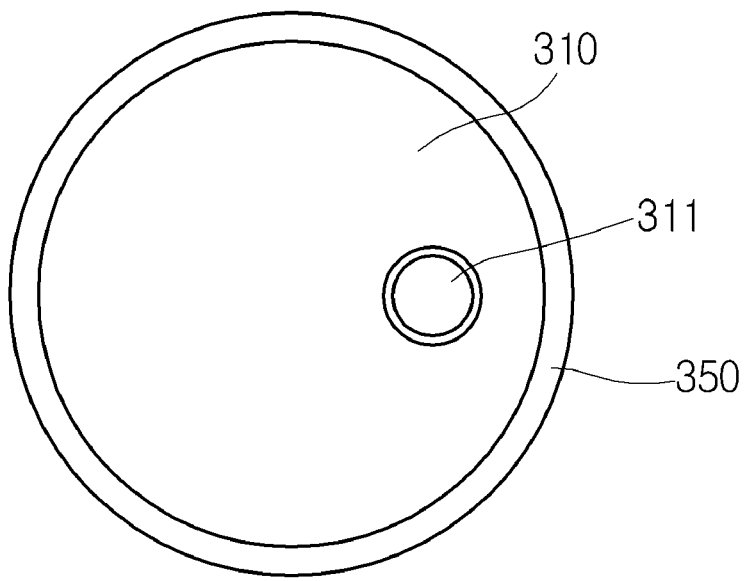

Then, FIG. 17 illustrates another shape of the tip electrode body 310, which is a structure in which the tip guide hole 311 is eccentrically positioned.

The tip electrode body 310 having the eccentric tip electrode body 310 processed is not generally used, but can be used according to the treatment environment. For example, if the stent delivery system 100 of the present disclosure has been inserted into the branch point where the blood vessel in the vascular system is divided in plural, when it is desired to move the tip electrode body 310 to the blood vessel in a desired direction, the guide wire 140 can be moved into the blood vessel more easily when it is positioned to face by rotating the eccentric tip guide hole 311 in the direction of the blood vessel.

In addition, in the present disclosure, as illustrated in FIGS. 18 to 21, the electrocautery tip 300 can be configured to further include a cauterization protrusion 370 formed at the outer circumferential surface of the tip electrode body 310. The cauterization protrusion 370 can be positioned in plural with predetermined intervals interposed therebetween at the outer circumferential surface of the tip electrode body 310.

It can be confirmed that FIG. 18 illustrates two cauterization protrusions 370 positioned at intervals of 180 degrees, FIG. 19 illustrates three cauterization protrusions 370 positioned at intervals of 120 degrees, and FIG. 20 illustrates four cauterization protrusions 370 positioned at intervals of 90 degrees, respectively, and this can guide the cauterization incision direction in advance when cauterizing the body tissue, such that the effect of minimizing the body tissue damage can also be expected. As in FIG. 21, the cauterization protrusion 370 can also be positioned in a spiral form rather than a straight-line form.

FIG. 24 is a partial perspective diagram illustrating the shape of the cauterization protrusion 370 illustrated in FIG. 20.

Of course, it is not limited to the disclosed form. The cauterization protrusion 370 can also be positioned at respective different intervals rather than the predetermined intervals, and other forms that can be inferred from the present disclosure can also be included in an embodiment of the present disclosure.

Meanwhile, although not illustrated in the drawing, as another example of the present disclosure, an interval between the plurality of cauterization protrusions 370 can be insulation-coated. In this case, since the tip electrode body 310 is insulation-coated, the cauterization of the body tissue is performed only for the cauterization protrusion 370, thereby reducing the cauterization range of the body tissue. Of course, although not illustrated in the drawing, it can be considered that the variable ring 350 is also insulation-coated according to the treatment environment.

The description of the structure and various embodiments of the present disclosure are as described above, and hereinafter, a stent delivery procedure according to the present disclosure will be described.

Figure 25:
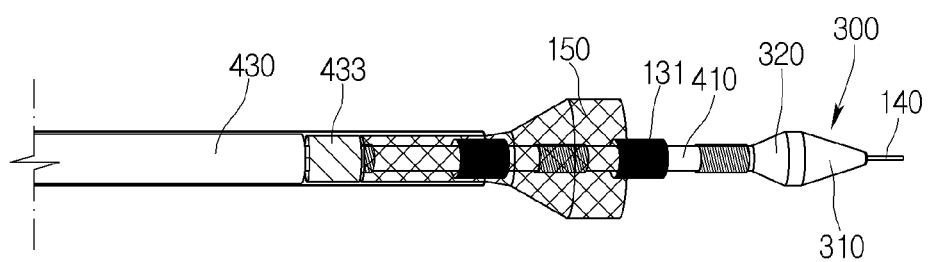
FIGS. 25 and 26 are diagrams illustrating a state where the stent is delivered in the present disclosure.
Figure 26:
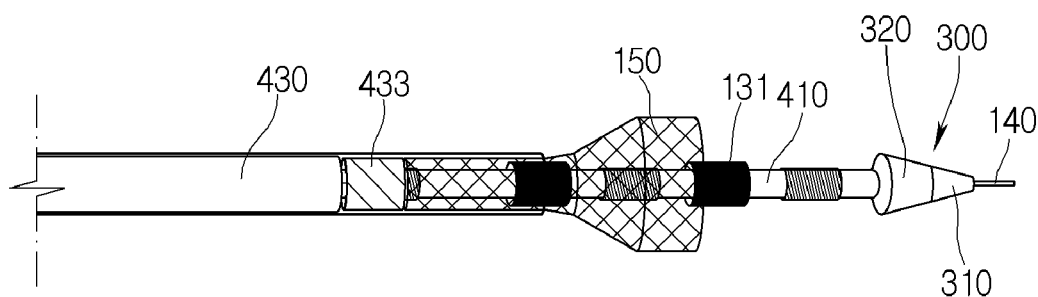

FIGS. 25 and 26 are diagrams illustrating a state where the stent is delivered in the present disclosure, and FIGS. 27 to 31 are diagrams illustrating the operation states of the present disclosure inside the human body tissue. Reference numerals necessary for describing the operation states will be described with reference to FIGS. 1 to 8, 25, and 26.

Figure 27:
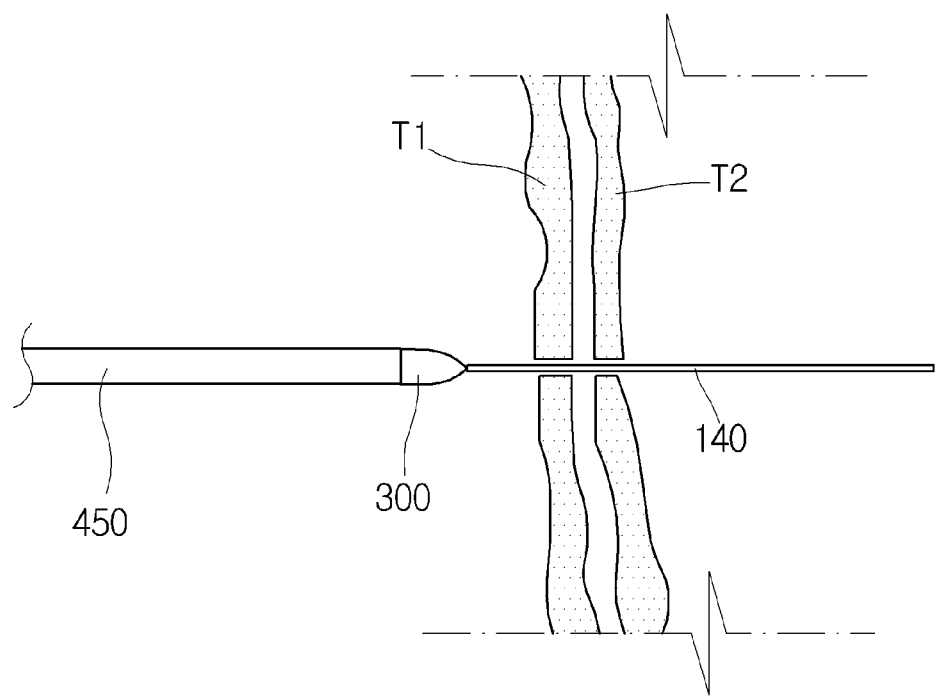
FIGS. 27 to 31 are diagrams illustrating the states where the present disclosure operates inside the human body tissue.
Figure 28:
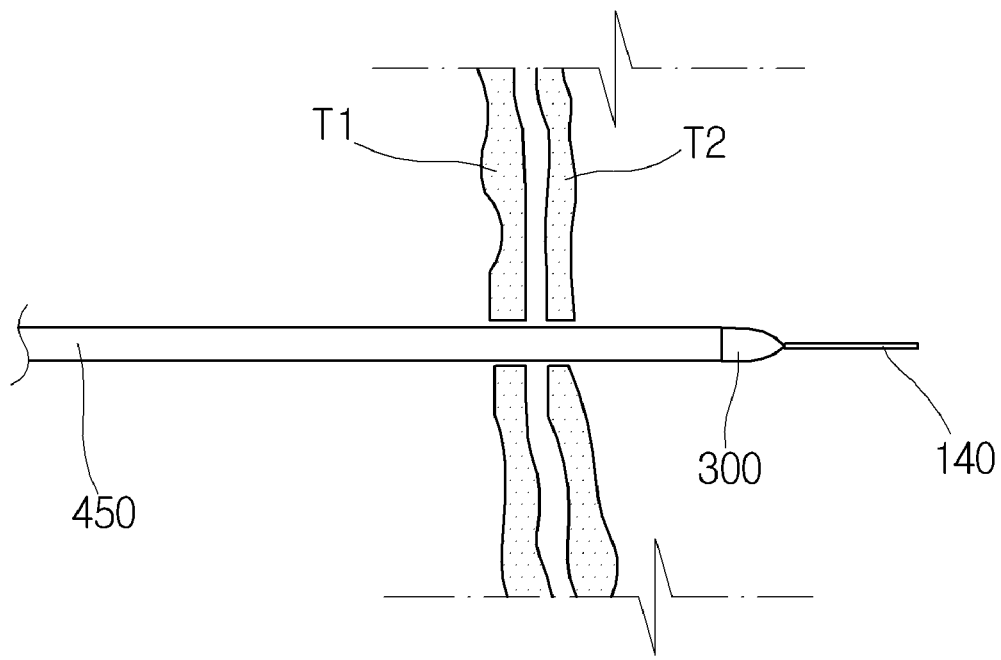

First, referring to FIG. 27, the practitioner first inserts the guide wire 140 in order to accurately specify the in-body position to be treated by the stent 150 and to guide the insertion path of the stent 150. That is, in FIG. 27, the guide wire 140 is inserted into the body tissue areas T1, T2 to be treated by the stent 150.

Next, when the guide wire 140 is positioned at the body tissue areas T1, T2 and the delivery direction of the stent 150 is set, the practitioner operates so that the end portion of the guide wire 140 is fitted into the tip guide hole 311 of the tip electrode body 310, and therefore, the guide wire 140 enters into the tip guide hole 311, and positioned by passing through the inner hole 411 of the first internal tube 410, a bar inner hole 491 of the movable bar 490, and a second inner hole 482 formed at the second grip body 481.

Thereafter, as in FIG. 15B, the practitioner grips the entire stent delivery system 100 and pushes it toward the guide wire 140. Therefore, the external tube 450 and the electrocautery tip 300 enter into the body tissue areas T1, T2.

At this time, the connector portion 200 receives a current from the external current source 110 and supplies the current to the tip electrode body 310 by the conductive line 120, thereby forming the cauterization hole in the body tissue by the heating reaction of the tip electrode body 310. Therefore, the external tube 450 can stably enter into the body tissue areas T1, T2.

Thereafter, the practitioner pulls out the guide wire 140 through the wire outlet 483 positioned at the rear end portion of the second inner hole 482 to remove the guide wire 140 from the body tissue areas T1, T2 and the inside of the stent delivery system 100.

Now, when positioning the stent 150 relatively adjacent to the treatment area, the practitioner grips the first grip portion 470 and the second grip portion 480, and pulls the first grip portion 470 in the direction of the second grip portion 480. At this time, since the first grip portion 470 is connected to the external tube 450 and the second grip portion 480 is connected to the second internal tube 430 by the movable bar 490, the external tube 450 is retracted while the first grip portion 470 moves along the movable bar 490.

Herein, since the end portion of the second internal tube 430 and the end portion of the first internal tube 410 are connected to each other, the first internal tube 410, which has been in place, is exposed to the outside of the external tube 450 as the external tube 450 is retracted.

Figure 29:
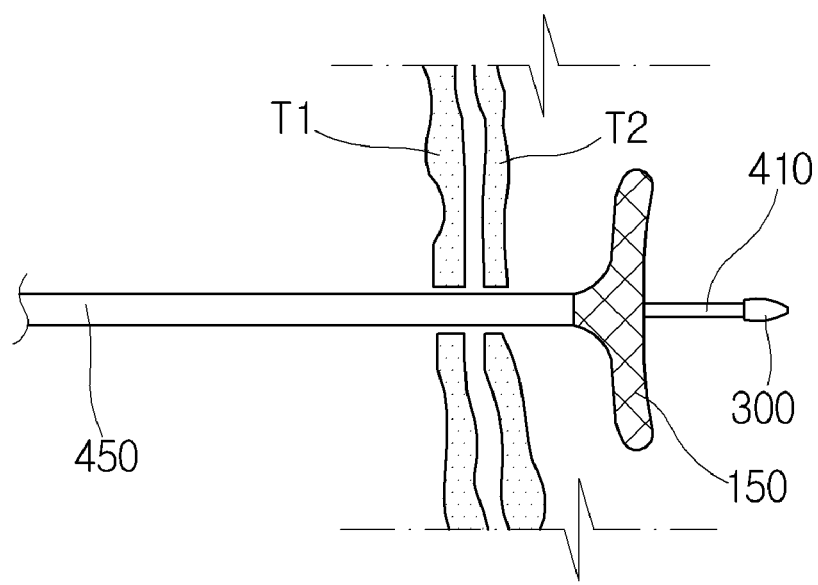

Referring to FIGS. 25, 26, and 29, as the first internal tube 410 is exposed to the outside of the external tube 450, the stent 150, which has been positioned in the stent space portion 130, is exposed to the body tissue areas T1, T2. The stent 150 is unfolded through self-expansion, and performs its function at the desired body tissue areas T1, T2.

Although FIGS. 27 to 31 illustrate a state where the stent 150 has been unfolded for the purpose of connecting between two areas T1, T2 of the body tissue, the present disclosure can also be used for expanding the circulatory system tube such as blood vessel, urethra, or lung in the circulatory system, such as blood vessel, urethra, or lung, which has been contracted or blocked.

Referring back to FIG. 29, as the external tube 450 retreats, the stent 150 is relatively pushed back by the sign block 433 positioned at the end portion of the second internal tube 430. That is, one end portion of the stent 150 is blocked and fixed by the sign block 433, and at this time, the external tube 450 moves backwardly, such that it is opened from the other end portion of the stent 150 to the outside of the external tube 450. Then, the stent 150 is positioned inside the body tissue areas T1, T2 and is self-expanded slowly.

Herein, the practitioner can confirm the current position of the stent inside the body tissue through the position identification of the sign block 433. For this purpose, the sign block 433 can be painted in a color that can be identified by the practitioner.

Figure 30:
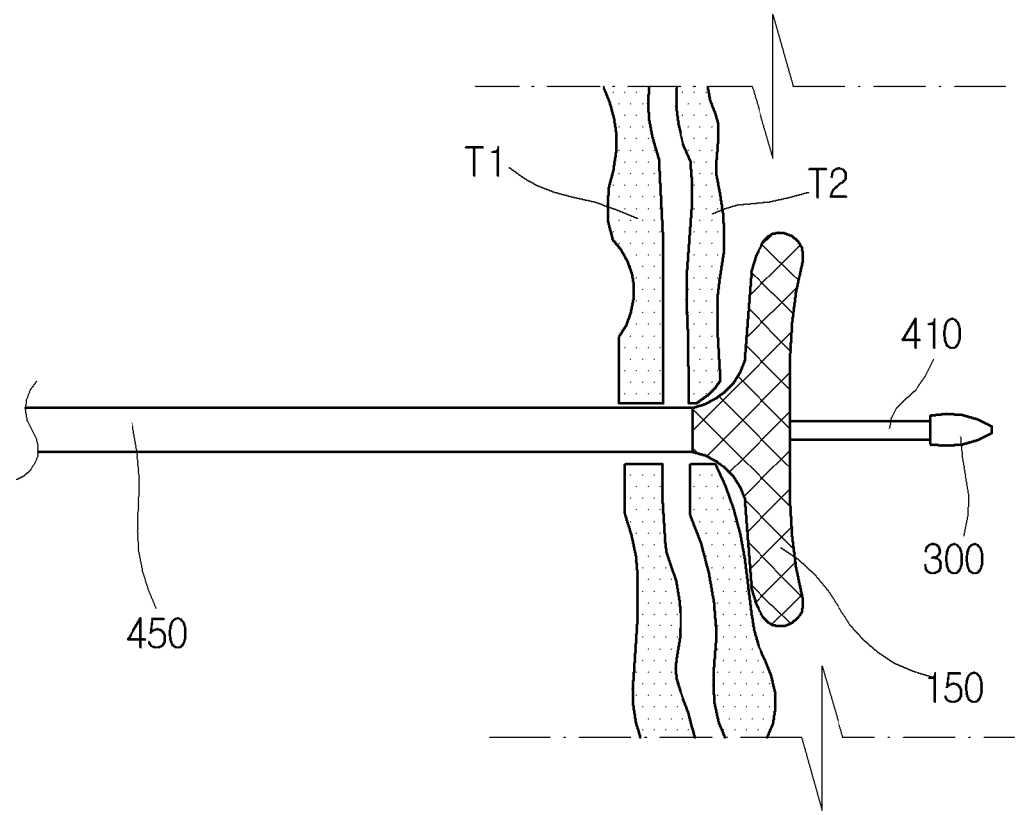

Thereafter, as in FIG. 30, the practitioner accurately positions the stent 150 in the desired body tissue by slightly pulling the stent 150 that has been partially expanded, and then further retreats the first grip portion 470 along the movable bar 490 so that the entire stent 150 is completely self-expanded.

Figure 31:
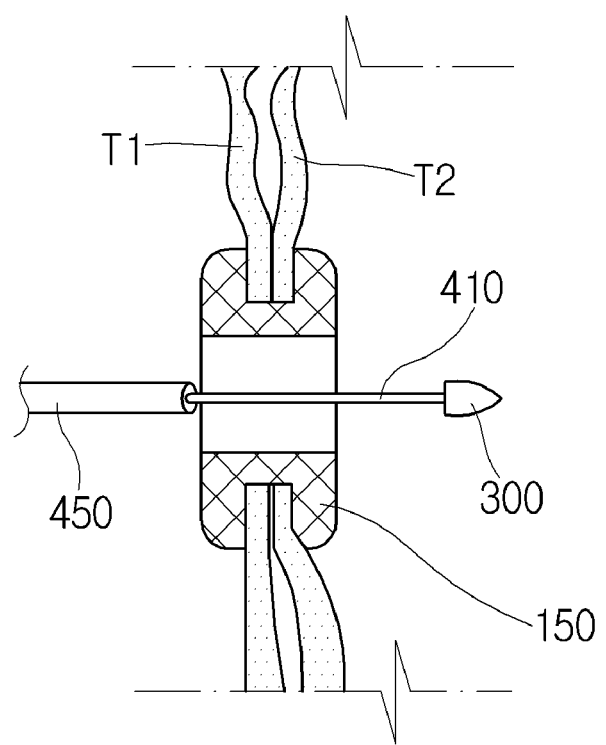

Then, as in FIG. 31, the stent treatment is completed by slowly pulling out the entire stent delivery system 100 and removing it from the body tissue.

The above description is merely a specific embodiment of the stent delivery system.

Therefore, it can be easily understood by those skilled in the art that the substitution and modification of the present disclosure can be made in various forms without departing from the scope of the disclosure as defined in the following claims.

INDUSTRIAL APPLICABILITY

The present disclosure relates to a stent delivery system, and there is an industrial applicability because it corresponds to a medical instrument technology field.

The invention claimed is:

1. A stent delivery system comprising:
a connector portion connected to an external current source;
an electrocautery tip connected to the connector portion by a conductive line; and
a delivery portion having a first side connected to the electrocautery tip and a second side connected to the connector portion, the conductive line being accommodated in the delivery portion for connecting the electrocautery tip and the connector portion,
wherein the delivery portion includes a stent space portion accommodating a stent and formed adjacent to the electrocautery tip inside the delivery portion, and the delivery portion is configured to move and supply the stent into a human body tissue,
wherein the electrocautery tip comprises:
a tip electrode body being made of a conductive material and having a tip guide hole formed therein, the tip electrode body having a first side portion with an outer circumferential surface tapered to be narrower in a direction towards a distal end of the electrocautery tip and a second side portion connected to the conductive line;
a tip insulator having a first side portion coupled to the second side portion of the tip electrode body and a second side portion connected to the delivery portion, the second side portion of the tip insulator having an outer circumferential surface tapered to be narrower in a direction opposite to the direction of the tip electrode body towards a proximal end of the electrocautery tip;
a coupling portion formed at a portion of the outer circumferential surface of the tip electrode body; and
a variable-sized ring configured to be coupled to the coupling portion to vary a maximum diameter of the tip electrode body,
wherein the coupling portion has a threaded outer surface, and the variable-sized ring has a threaded inner surface formed to correspond to the threaded outer surface of the coupling portion.

2. The stent delivery system of claim 1,
wherein the delivery portion comprises:
a first internal tube having the conductive line connected to the electrocautery tip positioned therein, and having an inner hole formed at an internal central side thereof;
a second internal tube positioned to surround a portion of an outer circumference of the first internal tube, and provided to be connected to the first internal tube to be integrally moved; and
an external tube positioned to surround the second internal tube.

3. The stent delivery system of claim 2,
wherein the first internal tube is an insulating coating material, and the conductive line is formed integrally with the first internal tube and positioned in a straight-line form along a longitudinal direction of the first internal tube.

4. The stent delivery system of claim 2,
wherein the first internal tube is an insulating coating material, and the conductive line is formed integrally with the first internal tube and positioned to be wound in a spiral direction along the outer circumference of the first internal tube.

5. The stent delivery system of claim 2,
wherein the first internal tube is an insulating coating material, and the conductive line is formed integrally with the first internal tube and positioned in a woven form along the outer circumference of the first internal tube.

6. The stent delivery system of claim 2,
wherein the delivery portion further comprises:
a first grip portion connected to the external tube; and
a second grip portion connected to the second internal tube by a movable bar,
wherein the connector portion is positioned on the second grip portion, and the first internal tube is positioned by passing through the movable bar and the second grip portion.

7. The stent delivery system of claim 1,
wherein one side of the tip insulator is tapered in a same direction as the tip electrode body.

8. The stent delivery system of claim 1,
wherein the tip electrode body and the tip insulator are provided in a triangular form that a side cross-sectional surface thereof is inclined in a same direction.

9. The stent delivery system claim 1,
wherein a portion of an outer surface of the variable-sized ring is tapered in a same direction as the tip electrode body.

10. The stent delivery system of claim 9,
wherein a portion of the outer surface of the variable-sized ring is tapered at an angle smaller than the tip electrode body.

11. The stent delivery system claim 1,
wherein an outer circumference of the variable-sized ring is rounded.

12. The stent delivery system of claim 11,
wherein a portion of the variable-sized ring has a different thickness.

13. The stent delivery system claim 1,
wherein the electrocautery tip further comprises:
an adhesion pad positioned on at least any one side of the coupling portion in order to prevent a gap between an inner circumference of the variable-sized ring and an outer circumference of the tip electrode body.

14. The stent delivery system of claim 1,
wherein the electrocautery tip further comprises:
a plurality of cauterization protrusions protruded from the outer circumferential surface of the tip electrode body,
wherein each of the plurality of cauterization protrusions is in a straight-line form or a curved form.

15. The stent delivery system claim 14,
wherein the outer circumferential surface of the tip electrode body between the plurality of cauterization protrusions is insulation-coated.

16. The stent delivery system of claim 2, further comprising a guide wire positioned in an inner hole of the first internal tube and the tip guide hole of the tip electrode body, and configured for guiding a moving direction of the electrocautery tip.

17. The stent delivery system of claim 6,
wherein the delivery portion further comprises:
an uneven portion formed along a longitudinal direction of the movable bar;
an elastic body positioned inside the first grip portion; and
a fixing block having one side contacting the elastic body and another side protruding to a first inner hole in order to be coupled to the uneven portion.

18. The stent delivery system of claim 17, wherein the fixing block comprises a rolling wheel.

19. The stent delivery system of claim 1, wherein the tip guide hole is eccentrically positioned inside the tip electrode body.

20. The stent delivery system of claim 6,
wherein the movable bar comprises:
an end block positioned inside the second grip portion; and
a stepped portion formed in a size smaller than the end block, and positioned in a through-hole of the connector portion.

* * * * *